US006284533B1

(12) United States Patent
Thomas

(10) Patent No.: US 6,284,533 B1
(45) Date of Patent: Sep. 4, 2001

(54) PLASMID-BASED VACCINE FOR TREATING ATHEROSCLEROSIS

(75) Inventor: Lawrence J. Thomas, Easton, MA (US)

(73) Assignee: AVANT Immunotherapeutics, Inc., Needham, MA (US)

( * ) Notice: Subject to any disclaimer, the term of this patent is extended or adjusted under 35 U.S.C. 154(b) by 0 days.

(21) Appl. No.: 09/171,969

(22) PCT Filed: May 1, 1997

(86) PCT No.: PCT/US97/07294

§ 371 Date: Oct. 28, 1998

§ 102(e) Date: Oct. 29, 1998

(87) PCT Pub. No.: WO96/34888

PCT Pub. Date: Nov. 7, 1996

Related U.S. Application Data

(63) Continuation-in-part of application No. 08/802,967, filed on Feb. 21, 1997.
(60) Provisional application No. 60/052,983, filed on May 1, 1996.

(51) Int. Cl.[7] .............................. C12N 18/88; A61K 48/00
(52) U.S. Cl. ...................... 435/320.1; 435/69.1; 435/455; 536/23.1; 536/23.4; 536/23.5; 514/44
(58) Field of Search ................................ 435/69.1, 320.1, 435/325, 455; 514/44, 2; 536/23.1, 23.4, 23.5

(56) References Cited

U.S. PATENT DOCUMENTS

| | | | |
|---|---|---|---|
| 5,242,687 | 9/1993 | Tykocinskli et al. | 424/93 |
| 5,338,829 | 8/1994 | Weiner et al. | 530/324 |
| 5,705,388 | 1/1998 | Couture et al. | 435/366 |

FOREIGN PATENT DOCUMENTS

| | | |
|---|---|---|
| 0 343 460 A2 | 11/1989 | (EP) . |
| WO 90/15627 | 12/1990 | (WO) . |
| WO 92/10203 | 6/1992 | (WO) . |
| WO 93/11782 | 6/1993 | (WO) . |
| WO 93/23076 | 11/1993 | (WO) . |
| WO 94/24567 | 10/1994 | (WO) . |
| WO 94/25060 | 11/1994 | (WO) . |
| WO 96/39168 | 12/1996 | (WO) . |

OTHER PUBLICATIONS

McCluskie et al. (Molecular Medicine, 5, pp. 287–300, 1999).*
Anderson, Nature, vol. 392, pp. 25–30, 1998.*
Verma, Nature, vol. 389, pp. 239–242, 1997.*
Shih et al. (Molecular Medicine Today, 1, 8, pp. 364–372, 1995).*
Feldman et al. (J. Clinical Investigation, 95, 6, 2662–71, 1995).*
Ada, G.L., *Fundamental Immunology*, 3rd ed., pp. 1309–1352 (W. E. Paul, ed.) (Raven Press, Ltd., New York, 1993).
Agellon, L.B. et al., *J. Biol. Chem.*, 266: 10796–10801 (1991).
Aitken, R.J. et al., *Brit. Med. Bull.*, 49: 88–99 (1993).
Albers et al., *Arteriosclerosis*, 4: 49–58 (1984).
Alexander et al., *Immunity*, 1: 751–761 (1994).
Barter et al., *J. Lipid Res.*, 21:238–249 (1980).
Bevilacqua et al., *J. Clin. Invest.*, 91: 379–387 (1993).
Bisgaier et al., *J. Lipid Res.*, 34:1625–1634 (1991).
Bisgaier et al., *J. Lipid Res.*, 32: 21–23 (1993).
Breslow, *Proc. Natl. Acad. Sci.* USA, 90: 8314–8318 (1993).
Brown et al., *Nature*, 348: 448–451 (1989).
Carlsson et al., *Biochem. J.*, 173: 723–737 (1978).
Casali et al., *Science*, 234: 476–479 (1986).
Castelli et al., *J. Am. Med. Assoc.*, 256: 2835–2838 (1986).
*Current Protocols in Immunology*, pp 3.11.1–3.11.15,3.12.01–3.12.14 (Coligan, J.E. et al., eds.) (John Wiley & Sons, New York, 1994).
Drayna et al., *Nature*, 327: 632–634 (1987).
Elridge et al., *Immunology of Proteins and Peptides V: Vaccines; Mechanisms, Designs, and Applications*, Attasi, M.Z., ed. (Plenum Press, New York, 1989), pp. 191–202.
Engelhard, Victor H., *Sci. Am.*, 54–60 (1994).
Etlinger et al., *Science*, 249: 423–425 (1990).
Etlinger H., *Immunol. Today*, 13: 52–55 (1992).
Farmer, J.A. et al., *Heart Disease. A Textbook of Cardiovascular Medicine*, 4th ed., pp 1125–1160 (Braunwald, E., ed.) (W. B. Saunders Co., Philadelphia, 1992).
Fielding et al., *J. Lipid Res.*, 36: 211–228 (1995).
Frondorf et al., *J. Immunol.* Methods, 172: 135–137 (1994).
Gavish et al., *J. Lipid Res.*, 28: 257–267 (1987).
Gaynor et al., *Atherosclerosis*, 110: 101–109 (1994).
*Genetic Engineering News*, 14: 44 (Aug. 1994).
Gordon et al., *N. Engl. J. Med.*, 321: 1311–1316 (1989).
Groener, J.E.M. et al., *Biochim. Biophys. Acta*, 1002: 93–100 (1989).
Green et al., *Cell*, 28: 477–187 (1982).
Ha et al., *Comp. Biochem. Physiol.*, 83B: 463–466 (1986).
Ha et al., *Biochim. Biophys. Acta*, 833: 203–211 (1985).
Havel et al., Introduction: Structure and metabolism of plasma lipoproteins', In *The Metabolic Basis of Inherited Disease*, 6th ed., pp. 1129–1138 (Scriver, C.R., et al., eds.) (McGraw–Hill, Inc., New York, 1989)

(List continued on next page.)

Primary Examiner—Dave T. Nguyen
(74) Attorney, Agent, or Firm—Leon R. Yankwich; Thomas R. Berka

(57) ABSTRACT

A plasmid-based vaccine is provided herein based on the combination of DNA segments coding for one or more B cell epitopes of cholesteryl ester transfer protein (CETP) and one or more broad range helper T cell epitopes. Administration of the plasmids as a vaccine to a vertebrate subject provides an immune response to the subject's endogenous CETP and modulation of CETP activity, leading to prevention or reversal of various manifestations of heart disease. The vaccines provide an advantageous strategy for the prevention or treatment of atherosclerosis.

20 Claims, 10 Drawing Sheets

OTHER PUBLICATIONS

Hayek et al., *J. Clin. Invest.*, 90: 505–510 (1992).
Hayek et al., *J. Clin. Invest.*, 91: 1665–1671 (1993).
Hesler et al., *J. Biol. Chem.*, 262: 2275–2282 (1987).
Hesler et al., *J. Biol. Chem.*, 263: 5020–5023 (1988).
Ikewaki et al., *J. Clin. Invest.*, 96: 1573–1581 (1995).
Inazu et al., *N. Engl. J. Med.*, 323: 1234–1238.
Jarnagin et al., *Proc. Natl. Acad. Sci. USA*, 84: 1854–1857 (1987).
Jiang et al., *J. Biol. Chem.*, 266: 4631–4639 (1991).
Jiang et al., *J. Biol. Chem.*, 268: 27406–27412 (1991).
Kligfield et al., *Am. Heart J.*, 112(3): 589–597 (1986).
Korn et al., *J. Mol. Biol.*, 65: 525–529 (1972).
Kotake et al., *J. Lipid Res.*, 37: 599–605 (1996).
Kushwaha et al., *J. Lipid Res.*, 34: 1285–1297 (1993).
Mabuchi, H. et al., *Annals N.Y. Acad. Sci.*, 748: 333–341 (1995).
Madden et al., *Ann. Rev. Immunol.*, 13: 587–622 (1995).
Mader, S.S., In *Human Biology*, $4^{th\ ed}$., pp. 83, 102 (Wm. C. Brown Publishers, Dubuque, Iowa, 1995).
Marguerite et al., *Mol. Immunol.*, 29: 793–800, 1992.
Marotti et al., *Nature*, 364: 73–75 (1993).
Mathews, C.K. and van Holde, K.E., *Biochemistry*, pp. 574–576, 626–630 (The Benjamin/Cummings Publishing Co., Redwood City, California, 1990).
Means and Feeney, *Bioconjugate Chem.*, 1: 2–12 (1990).
Mezdour et al., *Clin. Chem.* 40/4: 593–597 (1994).
Miller et al., *Am. Heart J.*, 113: 589–597 (1987).
Nagashima et al., *J. Lipid Res.*, 29: 1643–1649, 1988.
Nelson et al., *J. Clin. Invest.*, 91: 1157–1166 (1993).
Palker et al., *Proc. Natl. Acad. Sci.*, USA, 84: 2479–2483 (1987).
Panina–Bordignon et al., *Eur. J. Immonol.*, 19: 2237–2242 (1989).
Pruitt et al., *Transplantation*, 52: 868–873 (1991).
Pruitt et al., *J. Surg. Res.*, 50: 350–355 (1991).
Quig et al., *Ann. Rev. Nutr.*, 10: 169–193 (1990).
Quinet et al., *J. Clin. Invest.*, 85: 357–363 (1990).
Raju et al., Eur.*J. Immunol.*, 25: 3207–3214 (1995).
Roy, P. et al., *J. Lipid Res.*, 37: 22–34 (1996).
Rye et al., *J. Biol. Chem.*, 270: 189–196 (1995).
Sad et al., *Immunol.*, 76: 599–603 (1992).
Stern et al., *Nature*, 368: 215–221 (1994).
Suckling, Keith E., *Bio/Technology*, 12: 1379–1380 (1994).
Swenson et al., *J. Biol. Chem.*, 264: 14318–14326 (1989).
Swenson et al., *J. Biol. Chem.*, 263: 5150–5157 (1988).
Tall, A.R., *J. Lipid Res.*, 34: 1255–1274 (1993).
Tall, A.R., *J. Clin. Invest.*, 89: 379–384 (1990).
Tall, A.R., *J. Internal Med.*, 237: 5–12 (1995).
Talwar et al., *Proc. Natl. Acad. Sci. USA*, 91: 8532–8536 (1994).
Tam, J.P., *Proc. Natl. Acad. Sci.*, USA, 85: 5409–5413 (1988).
Tao et al., *Nature*, 362: 755–758 (1993).
Tato et al., *Arteriscler, Thromb. Vascular Biol.*, 15: 112–120 (1995).
*The Merck Manual of Diagnosis and Therapy*, $16^{th\ ed}$., (Merck & Company Inc., Rahway, New Jersey, 1992), pp. 22–23 (referring to infection prevention), pp. 114–115 (referring to bacterial diseases), pp. 1944–1947 (referring to health management of neonates, infants, and children).
Travis, *Science*, 262: 1974–1975 (1993).
Valmori et al., *J. Immunol.*, 149: 717–721 (1992).
Wang et al., *J. Biol. Chem.*, 270: 612–618 (1995).
Wang et al., *Science*, 254: 285–288 (1991).
Wang et al., *J. Biol. Chem.*, 268: 1955–1959 (1993).
Wang et al., *J. Biol. Chem.*, 267: 17487–17490 (1992).
Watanabe et al., *Proc. Natl. Acad. Sci. USA*, 89: 5103–5107 (1992).
Watson et al., *Molecular Biology of the Gene* $4^{th\ ed}$., (The Benjamin/Cummings Publishing Company, Inc., Melo Park, CA., 1987) p. 836.
Wedrychowski et al., *Biotechnology*, 11(4): 486–489 (1993).
Weisman et al., *Science*, 249: 146–151 (1990).
Whitlock et al., *J. Clin. Invest.*, 84: 129–137 (1989).
Yeh et al., *J. Immunol.*, 146: 250–256 (1991).
Yen et al.,*J. Clin. Invest.*, 83: 2018–2024 (1989).
Zannis et al., "Genetic mutations affecting human lipoproteins, their receptors, and their enzymes", *Advances in Human Genetics*, vol. 21, pp. 145–319 (Plenum Press, New York, NY., 1993).
Zegers et al., *Eur. J. Immunol.*, 23: 630–634 (1993).
Zhang et al., *Cell*, 1: 751–761 (1994).

* cited by examiner

FIGURE 5

```
GCGGCCGCC ATG CAG TAC ATC AAG GCC AAC TCC AAG TTC ATC GGC ATC ACG GAG
CGCCGGCGC TAC GTC ATG TAG TTC CGG TTG AGG TTC AAG TAG CCG TAG TGC CTC
  NotI     M   Q   Y   I   K   A   N   S   K   F   I   G   I   T   E
              |<                 TETANUS TOXOID                     >|

CGC TTC CCC CGC CCA GAT GGC CGA GAA GCT GTG GCC TAC AGG TTT GAG GAG GAT ATC
GCG AAG GGG GCG GGT CTA CCG GCT CTT CGA CAC CGG ATG TCC AAA CTC CTC CTA TAG
 R   F   P   R   P   D   G   R   E   A   V   A   Y   R   F   E   E   D   I
|<                         CETP (350-368)                                 >|

TTC GGT TTT CCC AAG CAC CTG CTG GTG GAT TTC CTG CAG AGC CTG AGC TAG CGGCCGC
AAG CCA AAA GGG TTC GTG GAC GAC CAC CTA AAG GAC GTC TCG GAC TCG ATC GCCGGCG
 F   G   F   P   K   H   L   L   V   D   F   L   Q   S   L   S   *
|<                         CETP (481-496)                        >| STOP  NotI
```

FIGURE 6

| RABBIT # | 1 | 2 | 3 | 4 | 5 | 6 | 7 | 8 | 10 | 11 | 12 | 13 | 14 |
|---|---|---|---|---|---|---|---|---|---|---|---|---|---|
| PRE 1 | (-11) | (-11) | (-11) | (-11) | (-11) | (-11) | (-11) | (-11) | X | X | X | X | X |
| PRE 2 | (-6) | (-6) | (-6) | (-6) | (-6) | (-6) | (-6) | (-6) | X | X | X | X | X |
| PRE 3 | 0 | 0 | 0 | 0 | 0 | 0 | 0 | 0 | X | X | X | X | X |
| CETP Vaccine | | | | | | | | | | | | | |
| BLEED 1 | 14 | 14 | 14 | 14 | 14 | 14 | 14 | X | X | X | X | X | X |
| BLEED 2 | 28 | 28 | 28 | 28 | 28 | 28 | 28 | X | X | X | X | X | X |
| CETP Vaccine | 28 | 28 | 28 | 28 | 28 | 28 | X | X | X | X | X | X | X |
| BLEED 3 | 44 | 44 | 44 | 44 | 44 | 44 | X | X | X | X | X | X | X |
| BLEED 4 | 57 | 57 | 57 | 57 | 57 | 57 | X | X | X | X | X | X | X |
| Tetanus | 66 | 66 | 66 | 66 | 66 | 66 | X | X | X | X | X | X | X |
| Tetanus | 91 | 91 | 91 | 91 | 91 | 91 | X | X | X | X | X | X | X |
| BLEED 5 | 99 | 99 | 99 | 99 | 99 | 99 | X | X | 99 | 99 | 99 | 99 | 99 |
| 0.25% Chol. | 99 | 99 | 99 | 99 | 99 | 99 | X | X | 99 | 99 | 99 | 99 | 99 |
| 0.5% Chol. | 112 | 112 | 112 | 112 | 112 | 112 | X | X | 112 | 112 | 112 | 112 | 112 |
| BLEED 6 | 128 | 128 | 128 | 128 | 128 | 128 | X | X | 128 | 128 | 128 | 128 | 128 |
| Tetanus | 128 | 128 | 128 | 128 | 128 | 128 | X | X | X | X | X | X | X |
| BLEED 7 | 147 | 147 | 147 | X | 147 | 147 | X | X | 147 | 147 | 147 | 147 | 147 |
| 0.25% Chol. | X | 154 | 154 | X | 154 | 154 | X | X | 154 | X | 154 | 154 | X |
| BLEED 8 | X | 163 | 163 | X | 163 | 163 | X | X | 163 | X | 163 | 163 | X |
| BLEED 9 | X | 177 | 177 | X | 177 | 177 | X | X | 177 | X | 177 | 177 | X |
| BLEED 10 | X | 198 | 198 | X | 198 | 198 | X | X | 198 | X | 198 | 198 | X |
| BLEED 11 | X | 212 | 212 | X | 212 | 212 | X | X | 212 | X | 212 | 212 | X |
| BLEED 12 | X | 220 | 220 | X | 220 | 220 | X | X | 220 | X | X | 220 | X |
| Termination | 148 | 220 | 220 | 148 | 220 | 220 | 30 | 2 | 220 | 148 | 219 | 220 | 147 |

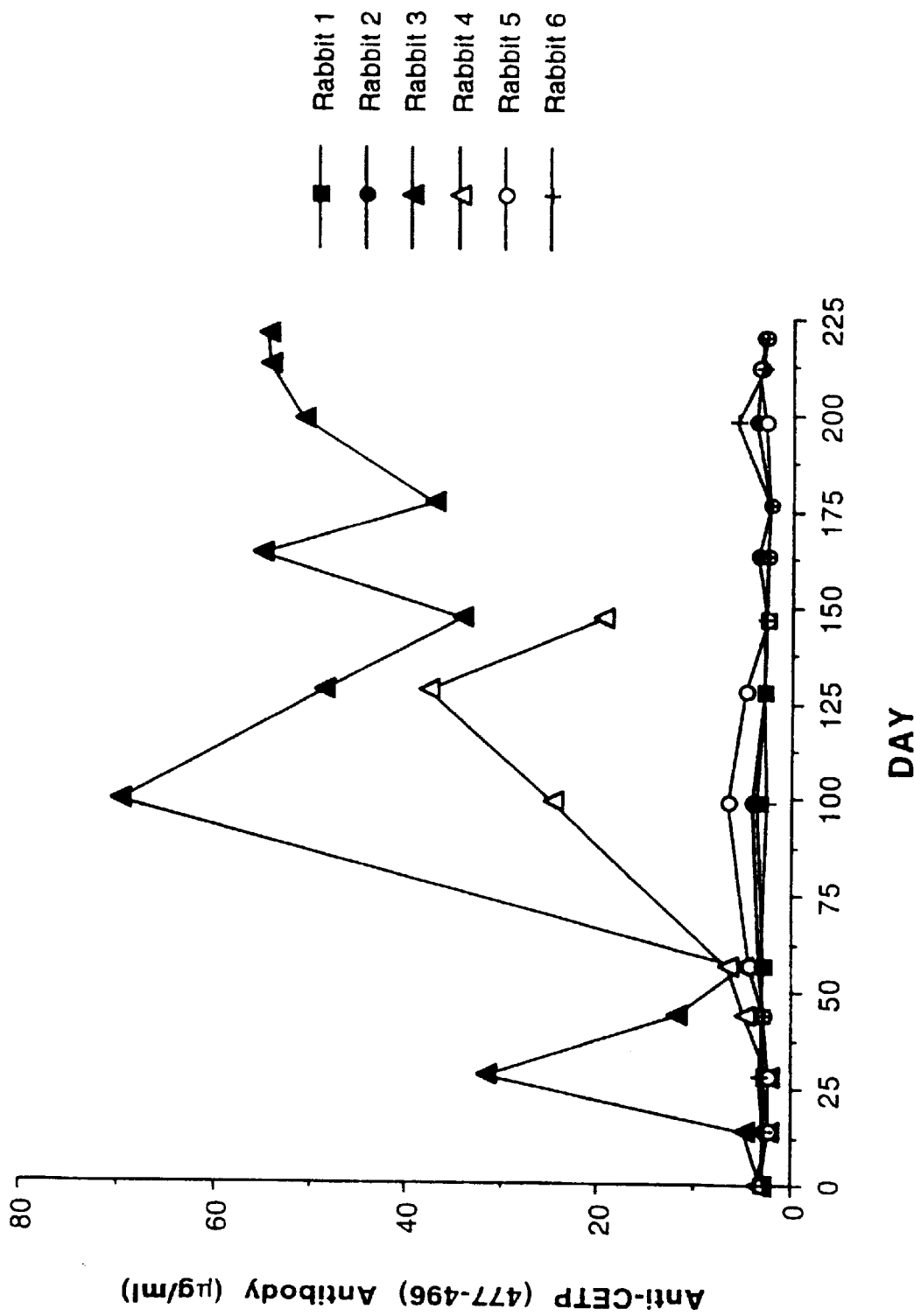

PLASMID-BASED VACCINE FOR TREATING ATHEROSCLEROSIS

CROSS-REFERENCE TO RELATED APPLICATION

This application is the United States national stage under 35 U.S.C. §371 of international application No. PCT/US97/07294, filed May 1, 1997, is which a continuation-in-part application of U.S. patent application Ser. No. 08/802,967, filed Feb. 21, 1997, now abandoned, which claims the benefit under 35 U.S.C. §119 of United States provisional application No. 60/052,983, filed May 1, 1996.

FIELD OF THE INVENTION

The present invention relates to the field of immunobiology and specifically to a plasmid DNA vaccine for controlling the activity or effect of cholesteryl ester transfer protein, or CETP, in the body.

BACKGROUND OF THE INVENTION

Cholesterol circulates through the body predominantly as components of lipoprotein particles (lipoproteins), which are composed of a protein portion consisting of one or more apolipoproteins (Apo) and various lipids, including phospholipids, triacylglycerols (triglycerides), cholesterol and cholesteryl esters. There are ten major classes of is apolipoproteins: Apo A-I, Apo A-II, Apo-IV, Apo B-48, Apo B-100, Apo C-I, Apo C-II, Apo C-III, Apo D, and Apo E.

Lipoproteins are classified by density and composition. High density lipoproteins (HDL), one function of which is to mediate transport of cholesterol from peripheral tissues to the liver, have a density usually in the range of approximately 1.063–1.21 g/ml. HDL contain various amounts of Apo A-I, Apo A-II, Apo C-I, Apo C-II, Apo C-III, Apo D, Apo E, as well as various amounts of lipids, such as cholesterol, cholesteryl esters, phospholipids, and triglycerides.

In contrast to HDL, low density lipoproteins (LDL), which generally have a density of approximately 1.019–1.063 g/ml, contain Apo B-100 in association with various lipids. In particular, the amounts of the lipids, cholesterol, and cholesteryl esters are considerably higher in LDL than in HDL, when measured as a percentage of dry mass. LDL are particularly important in delivering cholesterol to peripheral tissues.

Very low density lipoproteins (VLDL) have a density of approximately 0.95–1.006 g/ml and also differ in composition from other classes of lipoproteins, both in their protein and lipid content. VLDL generally have a much higher amount of triglycerides than do HDL or LDL and are particularly important in delivering endogenously synthesized triglycerides from liver to adipose and other tissues.

Even less dense than LDL, chylomicrons (density usually less than 0.95 g/ml) contain Apo A-I, Apo A-II, Apo B, Apo C-I, Apo C-II, and Apo C-III and mediate transport of dietary triglycerides and cholesteryl esters from the intestine to adipose tissue and the liver.

The features and functions of the various lipoproteins have been extensively studied. (See, for example, Mathews, C. K. and van Holde, K. E., Biochemistry, pp. 574–576, 626–630 (The Benjamin/Cummings Publishing Co., Redwood City, Calif., 1990); Havel, R. J., et al., "Introduction: Structure and metabolism of plasma lipoproteins", in The Metabolic Basis of Inherited Disease, 6th ed., pp. 1129–1138 (Scriver, C. R., et al., eds.) (McGraw-Hill, Inc., New York, 1989); Zannis, V. I., et a., "Genetic mutations affecting human lipoproteins, their receptors, and their enzymes", in Advances in Human Genetics. Vol. 21, pp. 145–319 (Plenum Press, New York, 1993)).

Decreased susceptibility to cardiovascular disease, such as atherosclerosis, has been generally correlated with increased absolute levels of circulating HDL and also with increased levels of HDL relative to circulating levels of lower density lipoproteins such as VLDL and LDL (see, for example, Gordon, D. J., et al., N. Engl. J Med., 321: 1311–1316 (1989); Castelli, W. P., et al., J. Am. Med. Assoc., 256: 2835–2838 (1986); Miller, N. E., et al., Am. Heart J., 113: 589–597 (1987); Tall, A. R., J. Clin. Invest., 89: 379–384 (1990); Tall, A. R., J. Internal Med., 237: 5–12 (1995)).

Cholesteryl ester transfer protein (CETP) mediates the transfer of cholesteryl esters from HDL to triglyceride-rich lipoproteins such as VLDL and LDL, and also the reciprocal exchange of triglycerides from VLDL to HDL (Tall, A. R., J. Internal Med., 237: 5–12 (1995); Tall, A. R., J. Lipid Res., 34: 1255–1274 (1993); Hesler, C. B., et al., J. Biol. Chem., 262: 2275–2282 (1987); Quig, D. W. et al., Ann. Rev. Nutr., 10: 169–193 (1990)). CETP may play a role in modulating the levels of cholesteryl esters and triglycerides associated with various classes of lipoproteins. A high CETP cholesteryl ester transfer activity has been correlated with increased levels of LDL-associated cholesterol and VLDL-associated cholesterol, which in turn are correlated with increased risk of cardiovascular disease (see, for example, Tato, F., et al., Arterioscler. Thromb. Vascular Biol., 15: 112–120 (1995)).

Hereinafter, LDL-C will be used to refer to total cholesterol, including cholesteryl esters and/or unesterified cholesterol, associated with low density lipoprotein. VLDL-C will be used to refer to total cholesterol, including cholesteryl esters and/or unesterified cholesterol, associated with very low density lipoprotein. HDL-C will be used to refer to total cholesterol, including cholesteryl esters and/or unesterified cholesterol, associated with high density lipoprotein.

All lipoproteins contain apolipoproteins that serve to maintain the structural integrity of lipoproteins and mediate the transport and metabolism of lipids by acting as ligands for specific receptors or co-factors of certain enzymes. In addition to CETP, other proteins, including hepatic lipase, lipoprotein lipase, lecithin:cholesterol acyltransferase (LCAT), LDL receptor, HDL-receptor (SR-B1) and chylomicron remnant receptor, are important in lipid transport and metabolism. Disruption in the function of these components may lead to dyslipidemia, the abnormal metabolism of plasma lipids, which in turn may contribute to the development of atherosclerosis.

The proteins, apolipoproteins, and lipoproteins described above participate in three pathways of lipid transport and metabolism: (1) the chylomicron pathway, (2) the VLDL-LDL pathway, and, (3) the reverse cholesterol pathway. Chylomicrons and chylomicron remnants transport dietary lipids from intestine to peripheral tissues, such as adipose tissue, and the liver. The VLDL-LDL pathway transports lipids from the intestine to peripheral tissues. In the reverse cholesterol pathway excess cholesterol, which cannot be degraded by most tissue, is esterified and delivered either directly in HDL or indirectly after exchange into other lipoprotein fractions to the liver for excretion from peripheral tissues. Specifically, nascent HDL, which is produced by the liver and intestine, enlarges and is transformed into HDL3 and then to HDL2 as cholesterol is acquired and esterified to cholesteryl ester. Cholesteryl esters (CE) can remain with HDL2 for transport and uptake by the liver or can be transferred to lower density lipoproteins, such as VLDL and LDL, by CETP in exchange for triglycerides. In the liver, HDL2 is depleted of triglycerides by hepatic lipase which converts HDL2 back to HDL3 for re-use. During this process CE may also be transferred to hepatocytes. In addition, some HDL may be directly taken up by hepatocytes (see, for example, Havel, R. J., et al., *The Metabolic Basis of Inherited Disease,* 6th ed., pages 1129–1138 (Scriver, C. R., et al., eds.) (McGraw-Hill, Inc., New York, 1989); Fielding, C. J., et al., *J. Lipid Res.,* 36: 211–228 (1995)).

Thus, the transfer of CE follows one of two pathways. First, lipoproteins may deliver cholesteryl esters to the liver for excretion, thus participating in the reverse cholesterol transport pathway. Second, cholesteryl esters may be recycled back to peripheral tissues.

When all components of these pathways are operating properly, dietary lipids are rapidly absorbed, transported, and stored or utilized. In the fasting state, lipids are efficiently transported to tissue, and cholesterol is recycled or excreted. Naturally occurring dyslipidemias, perhaps as a result of mutations of apolipoproteins, are often due to dysfunction of one or several of the components in the pathways described above (see, for example, Farmer, J. A. et al., *Heart Disease, A Textbook of Cardiovascular Medicine, 4th ed.,* pp. 1125–1160 (Braunwald, E., ed.) (W.B. Saunders Co., Philadelphia, 1992); Havel, R. J., et al, 1992; Zannis, V. I., et al, 1993). Chronic dietary excess of cholesterol may overwhelm normal mechanisms of cholesterol clearance from peripheral tissues, and atherosclerosis may result as evidenced by the development of lesions and blockage of blood flow in cardiovascular tissue.

A number of in vivo studies utilizing animal models or humans have indicated that CETP activity can affect the level of circulating cholesterol-containing HDL. Increased CETP-mediated cholesteryl ester transfer activity can produce a decrease in HDL-C levels relative to LDL-C and/or VLDL-C levels, which in turn is correlated with an increased susceptibility to atherosclerosis. For instance, injection of partially purified human CETP into rats (which normally lack CETP activity), was shown to result in a shift of cholesteryl ester from HDL to VLDL, consistent with CETP-promoted transfer of CE from HDL to VLDL (see, Ha, Y. C., et al., *Biochem. Biophys. Acta,* 833: 203–211 (1985); Ha, Y. C., et al., *Comp. Biochem. Physiol.,* 83B: 463–466 (1986); Gavish, D., et al., *J. Lipid Res.,* 28: 257–267 (1987)). In addition, transgenic mice expressing human CETP were reported to exhibit a significant decrease in the level of cholesterol associated with HDL (see, for example, Hayek, T., et al., *J. Clin. Invest.,* 90: 505–510 (1992); Breslow, J. L., et al., *Proc. Natl. Acad. Sci. USA,* 90: 8314–8318 (1993)). Furthermore, whereas wild-type mice are normally highly resistant to atherosclerosis (Breslow, J. L., et al., *Proc. Natl. Acad. Sci. USA,* 90: 8314–8318 (1993)), transgenic mice expressing a simian CETP were reported to have an altered distribution of cholesterol associated with lipoproteins, namely, elevated levels of LDL-C and VLDL-C and decreased levels of HDL-C (Marotti, K. R., et al., *Nature,* 364: 73–75 (1993)). Such transgenic mice expressing simian CETP also were more susceptible to dietary-induced severe atherosclerosis compared to non-expressing control mice and developed lesions in their aortas which were significantly larger in area than found in control animals and more typical of those found in atherosclerosis (Marotti et al., 1993). Intravenous infusion of anti-human CETP monoclonal antibodies (Mab) into hamsters and rabbits inhibited CETP activity in vivo and resulted in significantly increased levels of HDL-C levels, decreased levels of HDL-triglycerides, and increased HDL size, again implicating a critical role for CETP in the distribution of cholesterol in circulating lipoproteins (see, Gaynor, B. J., et al., *Atherosclerosis,* 110: 101–109 (1994) (hamsters); Whitlock, M. E., et al., *J. Clin. Invest.,* 84: 129–137 (1989) (rabbits)).

The role of CETP activity has also been studied in humans. For example, in certain familial studies in Japan, individuals that were homozygous for non-functional alleles of the CETP gene had no detectable CETP activity. Virtually no atherosclerotic plaques were exhibited by these individuals, who also showed a trend toward longevity in their families (see, for example, Brown, M. L., et al., *Nature,* 342: 448–451 (1989); Inazu, A., et al., *New Engl. J. Med.,* 323: 1234–1238 (1990); Bisgaier, C. L., et al., *J. Lipid Res.,* 32: 21–23 (1991)). Such homozygous CETP-deficient individuals also were shown to have an anti-atherogenic lipoprotein profile as evidenced by elevated levels of circulating HDL rich in cholesteryl ester, as well as overall elevated levels of HDL, and exceptionally large HDL, i.e., up to four to six times the size of normal HDL (Brown, M. L., et al., 1989, supra at p. 451).

The above studies indicate that CETP plays a major role in transferring cholesteryl ester from HDL to VLDL and LDL, thereby altering the relative profile of circulating lipoproteins to one that is associated with an increased risk of cardiovascular disease (i.e., decreased levels of HDL-C and increased levels of VLDL-C and LDL-C). Marotti et al. (*Nature,* 364: 73–75 (1993)) interpreted their data as indicating that a CETP-induced alteration in cholesterol distribution was the principal reason that arterial lesions developed more rapidly in transgenic, CETP-expressing mice than in non-transgenic control mice when both groups were fed an atherogenic diet.

CETP isolated from human plasma is a hydrophobic glycoprotein having 476 amino acids and a relative molecular weight of approximately 66,000 to 74,000 daltons on sodium dodecyl sulfate (SDS)-polyacrylamide gels (Albers, J. J., et al., *Arteriosclerosis,* 4: 49–58 (1984); Hesler, C. B., et al., *J. Biol. Chem.,* 262: 2275–2282 (1987); Jarnagin, S. S., et al., *Proc. Nati. Acad. Sci. USA,* 84: 1854–1857 (1987)). A cDNA encoding human CETP has been cloned and sequenced (Drayna, D., et al., *Nature,* 327: 632–634 (1987)). CETP has been shown to bind cholesteryl esters (CE), triglycerides (TG), phospholipids (Barter, P. J. et al., *J. Lipid Res.,* 21:238–249 (1980)), and lipoproteins (see, for example, Swenson, T. L., et al., *J. Biol. Chem.,* 264: 14318–14326 (1989)). More recently, the region of CETP defined by the carboxyl terminal 26 amino acids, and in particular amino acids 470 to 475, has been shown to be especially important for neutral lipid binding involved in neutral lipid transfer (Hesler, C. B., et al., *J. Biol. Chem.,* 263: 5020–5023 (1988)), but not phospholipid binding (see, Wang, S., et al., *J. Biol. Chem.,* 267: 17487–17490(1992); Wang, S., et al., *J. Biol. Chem.,* 270: 612–618 (1995)).

It follows from current research that increased levels of CETP activity may be predictive of increased risk of cardiovascular disease. Endogenous CETP activity is thus an attractive therapeutic target for modulating the relative levels of lipoproteins to prevent or inhibit the development of or to promote regression of cardiovascular diseases such as atherosclerosis.

It would be useful, therefore, to develop the means and methods to control or modulate endogenous CETP activity to prevent or treat cardiovascular disease. Preferably, the modulation of endogenous CETP activity in a human or animal would be accomplished by administering to the subject a pharmaceutical composition that is specific for CETP, does not require large quantities, does not require continuous or frequently repeated dosing, and also does not produce untoward side effects.

SUMMARY OF THE INVENTION

A DNA plasmid-based vaccine is described that comprises a plasmid DNA molecule containing a DNA sequence encoding an immunogenic fusion polypeptide that, when administered to a human or animal subject, will induce the production of autoantibodies specifically reactive with endogenous CETP. Such antibodies inhibit endogenous CETP activity or remove CETP from circulation (clearance), promote the formation and maintenance of an anti-atherogenic serum lipoprotein profile (for example, increased HDL levels and decreased LDL levels), and/or inhibit the development of atherosclerotic lesions.

The immunogenic fusion polypeptide encoded on a plasmid as described herein comprises a T cell epitope portion and a B cell epitope portion. A T cell epitope portion encoded on the plasmid of this invention comprises a non-endogenous CETP protein, or fragment thereof, that contains a broad range or "universal" helper T cell epitope which binds the antigen presenting site of multiple (i.e., 2, 3, 4, 5, 6 or more) class II major histocompatibility (MHC) molecules and can form a tertiary complex with a T cell antigen receptor, i.e., MHC:antigen:T cell antigen receptor. By "non-endogenous CETP protein" is meant a protein which is not the endogenous CETP of the individual who is to be administered a plasmid of this invention. Such non-endogenous CETP proteins, or fragments thereof, useful as T cell epitope portions of the immunogenic fusion polypeptide encoded by plasmids of this invention include tetanus toxoid (particularly peptides of tetanus toxoid having amino acid sequences of amino acids 2–15 of SEQ ID NO:7 and amino acid sequence of SEQ ID NO:10); diphtheria toxin (particularly peptides having amino acid sequences of amino acids 271–290, 321–340, 331–350, 351–370, 411–430, and 431–450 of SEQ ID NO:9); class II MHC-associated invariant chain; influenza hemagglutinin T cell epitope; keyhole limpet hemocyanin (KLH); a protein from known vaccines including pertussis vaccine, the Bacile Calmette-Guerin (BCG) tuberculosis vaccine, polio vaccine, measles vaccine, mumps vaccine, rubella vaccine, and purified protein derivative (PPD) of tuberculin; and also synthetic peptides which bind the antigen presenting site of multiple class II histocompatibility molecules, such as those containing natural amino acids described by Alexander et al. (*Immunity*, 1: 751–761 (1994)). When attached to a CETP B cell epitope portion, the T cell epitope portion enables the immunogenic fusion polypeptide to break tolerance in order for antibodies to be made that react with endogenous CETP. By "breaking tolerance" is meant forcing an organism to mount an immune response to a protein, such as endogenous CETP, that the organism does not normally find immunogenic.

The B cell epitope portion of an immunogenic fusion polypeptide encoded on a plasmid of this invention comprises the amino acid sequence of the endogenous CETP, or fragment thereof, of the same species as the individual who will be administered the plasmid; the CETP, or fragment thereof, from a species different from the individual who will be administered the plasmid; or a synthetic amino acid sequence which elicits antibodies that bind to endogenous CETP. Such a B cell epitope portion useful in the plasmid-based CETP vaccine of this invention is encoded by a DNA sequence of at least 15 nucleotides in length.

In one embodiment of the invention, a DNA plasmid contains a structural coding sequence for an immunogenic fusion polypeptide wherein the structural coding sequence comprises a DNA sequence encoding a tetanus toxoid polypeptide (such as nucleotides 13–54 of SEQ ID NO:5) as the T cell epitope portion linked in the same reading frame with DNA sequences (such as nucleotides 55–159 of SEQ ID NO:5) encoding amino acids 350–368 and 481–496 of the amino acid sequence of mature rabbit CETP (SEQ ID NO:2) as the B cell epitope portion. In a preferred embodiment, a DNA plasmid of this invention encodes a structural coding sequence for an immunogenic fusion polypeptide wherein the structural coding sequence comprises a DNA sequence encoding a tetanus toxoid polypeptide (such as in nucleotides 13–54 of SEQ ID NO:5) as the T cell epitope portion of the immunogenic fusion polypeptide linked in the same reading frame with DNA sequences, such as nucleotides 1045–101 and 1381–1428 of SEQ ID NO:3 encoding, respectively, amino acids 349–367 and 461–476 of the amino acid sequence of mature human CETP (SEQ ID NO:4) as the B cell epitope portion of the immunogenic fusion polypeptide.

The immunogenic fusion polypeptides of the invention are expressed from the plasmids of this invention at sufficient levels and for a sufficient period of time to elicit production of autoantibodies that react specifically with endogenous CETP and that serve to decrease or inhibit CETP-mediated atherogenesis as evidenced by an anti-atherogenic serum lipoprotein profile and/or an inhibition in the development of atherosclerotic lesions.

Expression of the immunogenic fusion protein is directed by a promoter or promoter/enhancer sequence that can direct efficient transcription in mammalian cells, particularly skeletal muscle cells. Such promoter/enhancer sequences include, but are not limited to, human cytomegalovirus (CMV) promoter/enhancer sequence, adenovirus promoter/enhancer sequence, and β-actin promoter/enhancer sequence.

In addition, a plasmid of this invention may or may not encode an amino terminal secretion signal sequence linked to the immunogenic fusion polypeptide. Preferably, a plasmid of this invention encodes an immunogenic fusion polypeptide that does not contain an amino terminal secretion signal sequence.

In another preferred embodiment, a plasmid of this invention also includes a poly A signal sequence located 3' to the structural coding sequence of the immunogenic fusion polypeptide.

Thus, a preferred plasmid of this invention consists essentially of a promoter/enhancer sequence which is operably linked to a DNA sequence encoding an immunogenic fusion polypeptide comprising a T cell epitope portion and a B cell epitope portion which induces an individual receiving the plasmid to produce an immune response that results in the inhibition of the activity of endogenous CETP.

The DNA plasmids of this invention may be administered by any means normally used to administer plasmid-based vaccines to humans or animals, provided the mode of administration results in expression of the immunogenic fusion polypeptide and production of antibodies which specifically react with (i.e., bind) the endogenous CETP. Preferably, the DNA plasmids are administered intramuscularly or intradermally.

BRIEF DESCRIPTION OF THE DRAWINGS

FIG. 5 shows the nucleotide sequence of a DNA insert encoding a tetanus toxoid fragment and two CETP B cell epitopes, as a fusion polypeptide, inserted under the control of the CMV promoter/enhancer in plasmid pCMV-CETP/TT. The corresponding, single-letter abbreviation of the amino acid sequence for the encoded immunogenic fusion polypeptide and the location of NotI restriction endonuclease cleavage sites in the DNA insert are also depicted.

FIG. 6 shows an outline of the daily protocol used for testing the plasmid-based vaccine pCMV-CETP/TT in rabbits #1–#8 and #10–#14 (indicated as numbers at top of table columns) under differing dietary conditions. The day on which a particular step (row) of the protocol was carried out on a particular rabbit (column) is indicated in each box. Rabbits #1–#8 were injected with 50 μg of pCMV-CETP/TT as a plasmid-based CETP vaccine and 50 μg of pCMV-LUC as an internal control and reporter on indicated days (see rows labeled "CETP Vaccine"). The first injection of the plasmids to rabbits #1–#8 occurred on Day 0. Rabbits #10–#14 were control rabbits which did not receive either of the plasmids (negative control animals). Boxes in rows labeled "PRE 1", "PRE 2", or "PRE 3" indicate days (designated as negative numbers in bold and in parentheses) on which blood samples ("prebleeds") were obtained from rabbits prior to the first administration of the plasmids. "PRE 3" also indicates that blood samples were drawn on the same day as and prior to the first injection of plasmids pCMV-CETP/TT and pCMV-CETP/TT DNA into rabbits #1–#8. Boxes in rows labeled "BLEED 1"–"BLEED 12" indicate those days (in bold) on which blood samples were obtained from rabbits after the first injection of plasmid DNA into rabbits #1–#8 on Day 0. Boxes in rows labeled "Tetanus" indicate the day on which a rabbit received an intramuscular injection of an alum-adsorbed vaccine preparation of tetanus toxoid. Boxes in rows labeled "0.25% Chol." and "0.5% Chol." indicate the day on which a particular rabbit was placed on a rabbit chow diet supplemented with 0.25 % (w/w) cholesterol or 0.5 % (w/w) cholesterol, respectively. Boxes containing an "X" indicate that a particular rabbit was either not in the particular protocol step designated by the row or that the animal had been sacrificed. Boxes in rows labeled "Termination" indicate the day on which each rabbit was sacrificed.

FIG. 10 is a graph showing concentration (μg/ml) of anti-$CETP_{477-496}$ antibodies in rabbit plasma samples taken as described in FIG. 6. Plasma was assayed from rabbit #1 (filled square), rabbit #2 (filled circle), rabbit #3 (filled triangle), rabbit #4 (open triangle), rabbit #5 (open circle), and rabbit #6 (cross).

DETAILED DESCRIPTION OF THE INVENTION

Figure 1:
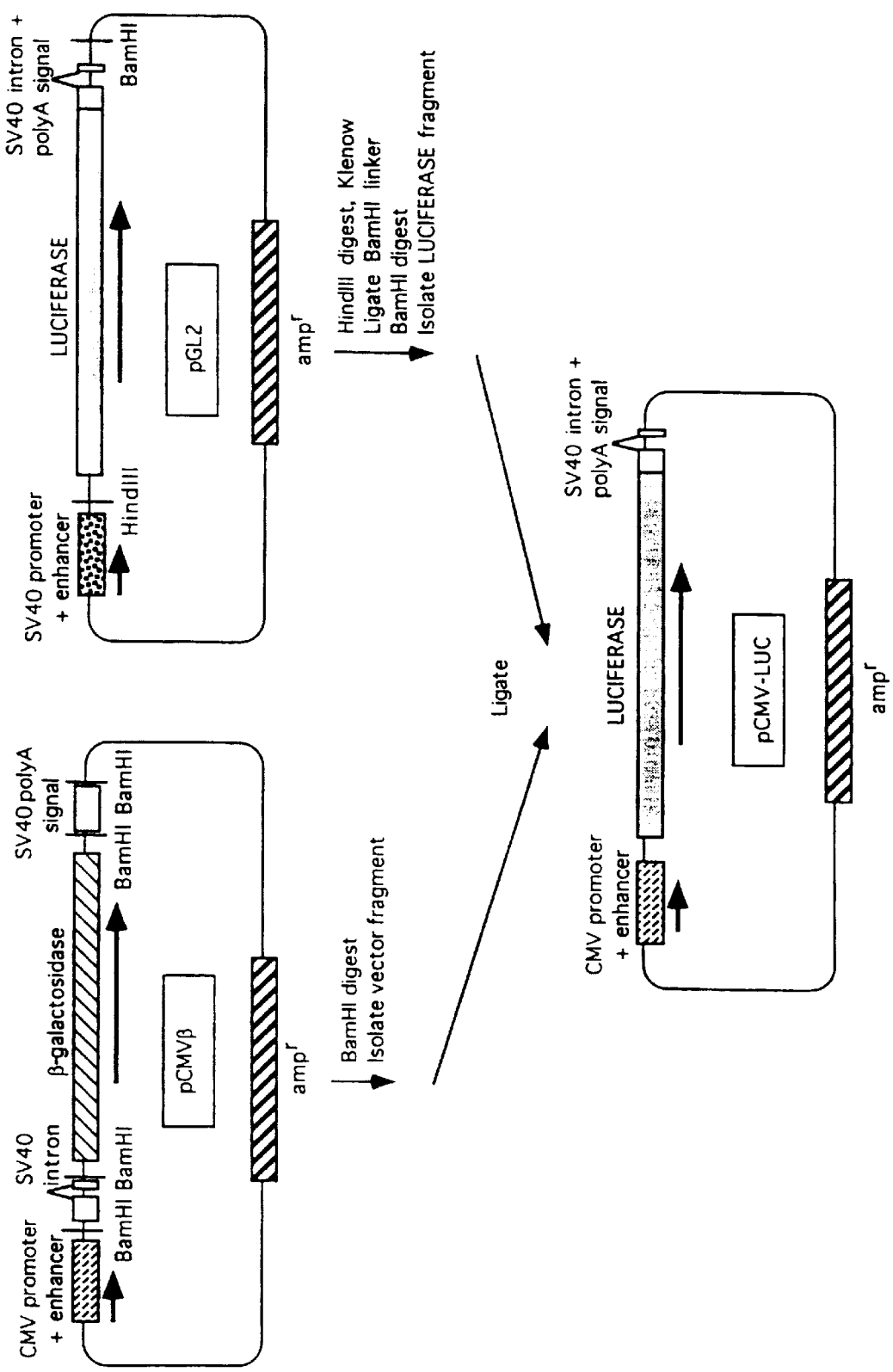
FIG. 1 is a diagram showing the construction of plasmid pCMV-LUC which contains a luciferase gene the transcription of which is under the control of a CMV promoter and enhancer.

The instant invention provides a strategy for the inhibition or prevention of cardiovascular disease, such as atherosclerosis, by modulating CETP activity, either by inhibiting CETP activity by antibody binding or clearing CETP activity from the circulatory system (or both). The modulation of endogenous CETP activity is accomplished using a plasmid-based vaccine. The DNA plasmids described herein encode immunogenic fusion polypeptides which when expressed in vivo elicit the production of autoantibodies to inhibit and/or clear circulating endogenous CETP activity. The present invention also provides a method for immunizing a vertebrate, such as a human, to elicit an antibody response to its endogenous CETP and thereby modulate CETP activity.

The various designations for lipids, lipoproteins, and apolipoproteins referred to below are the same as described in the Background above. As noted above, CETP plays a significant role in the transport and distribution of CE and TG between lipoproteins HDL and LDL. A decreased CETP activity produces a non-atherogenic lipoprotein profile or decreases the development of atherosclerosis (see, for example, Mabuchi et al., *Acad. Sci.*, 748: 333–341 (1995); Inazu et al., *New Eng. J. Med.*, 323: 1234–1238 (1990); Gaynor et al., *Arherosclerosis*, 110: 101–109 (1994); Whitlock et al., *J. Clin. Invest.*, 84: 129–137 (1989)). Conversely, increased CETP activity produces an atherogenic lipoprotein profile and induces atherosclerosis. The overexpression of CETP in transgenic animals decreases HDL levels and accelerates atherosclerosis (Agellon et al., *J. Biol. Chem.*, 266: 10796–10801 (1991); Marotti et al., *Nature*, 364:

73–75 (1993)), and the administration of CETP to experimental animals can lead to elevated levels of VLDL-C and LDL-C and a relative decrease in the level of HDL-C (Groener et al., *Biochim. Biophys. Acta,* 1002: 93–100 (1989); Ha et al., *Biochim. Biophys. Acta,* 833: 203–210 (1985)). Thus, inhibition of CETP activity is a desirable clinical outcome that will help prevent atherosclerosis, and inhibition of CETP activity is an appropriate strategy for promoting a physiological state associated with prevention and treatment of cardiovascular disease.

In the invention described herein, plasmid-based vaccines are provided for producing autoantibodies directed to endogenous CETP. Specifically, DNA plasmids are described which are administered (for example, by intramuscular injection or intradermal ballistic administration) to an individual. The administered DNA plasmids encode and direct the production of immunogenic fusion polypeptides which exhibit one or more broad range or "universal" helper T cell epitopes and also one or more B cell epitopes of CETP. Such immunogenic polypeptides elicit the production of autoantibodies that react specifically with (i.e., bind to) CETP in the individual (endogenous CETP). The production of anti-CETP antibodies promotes a physiological state associated with decreased risk of cardiovascular disease. The beneficial modulation of CETP activity produced by the DNA vaccines is evidenced by a significantly decreased or eliminated CETP activity; by an anti-atherogenic lipoprotein profile (for example, an increase in the level of HDL or HDL-C compared to LDL, LDL-C, VLDL, or VLDL-C); or by an inhibition (including prevention) or decrease in the development of atherosclerotic lesions in cardiovascular tissue, such as the aorta.

Design of DNA Plasmid Vaccine for Modulation of Endogenous CETP

Many small peptides only become antigenic when coupled to larger immunogenic carrier proteins (see, Etlinger, *Immunol. Today,* 13, 52–55 (1992)). The carrier protein is understood to provide epitopes recognized by helper T cells. Thus, although self-antigens, such as B cell epitopes of endogenous proteins, are generally not immunogenic, recent evidence has indicated that self-antigens can be made more immunogenic by linking them to one or more epitopes recognized by helper T cells of the host's immune system. Such immunogenic polypeptides containing one or more helper T cell epitopes and B cell epitopes of a particular endogenous protein may elicit production of autoantibodies that specifically react with the particular endogenous protein. For example, a fragment of human chorionic gonadotropin (hCG) has been conjugated to carrier proteins to produce a peptide vaccine to elicit autoantibodies reactive with hCG (see, Ada, G. L., in *Fundamental Immunology,* 3rd ed W. E. Paul, ed. (Raven Press, Ltd., New York, 1993) pp. 1309–1352; Aitken et al., *Brit. Med Bull.,* 49: 88–99 (1993)). This peptide vaccine consisted of a heterospecies dimer of the alpha-subunit of ovine luteinizing hormone and the beta-subunit of hCG conjugated to either of two immunogenic carrier proteins, tetanus toxoid (TT) or diphtheria toxoid (DT) (Talwar et al., *Proc. Natl. Acad Sci.,* 91: 8532–8536 (1994)). In addition, a peptide vaccine including the C-terminal portion of human CETP and a T cell epitope from tetanus toxoid was shown to elicit an anti-CETP antibody response and to alter CETP activity in rabbits, as described in commonly assigned, copending U.S. application Ser. No. 08/432,483, filed May 1, 1995, incorporated herein by reference.

Broad Range T Cell Epitopes

The DNA plasmids described herein comprise a DNA sequence encoding an immunogenic fusion polypeptide comprising a T cell epitope portion and a B cell epitope portion. The helper T cell epitope portion (or simply, "T cell epitope portion") encoded on a plasmid of this invention comprises a non-endogenous CETP protein, or fragment thereof, that contains a "universal" or "broad range" T cell epitope which binds antigen presenting sites of multiple (two or more) class II major histocompatibility (MHC) molecules and can form a tertiary complex with a T cell antigen receptor, i.e., MHC:antigen:T cell antigen receptor, which is the functional unit of T cell epitope recognition. Thus, "universal" or broad range T cell epitopes useful in this invention bind the antigen presenting site of multiple class II MHC molecules and serve to activate helper T cells which, in turn, stimulate B cell growth and differentiation, leading to the secretion of specific antibodies. Preferably, a universal or broad range T cell epitope encoded by a plasmid of this invention binds the antigen presenting site of three or more different class II MHC molecules, such as three different allelic class II MHC molecules, found in the human population. More preferably, a universal or broad range T cell epitope encoded on a plasmid of this invention binds the antigen presenting site of four or more different class II MHC molecules. Most preferably, a universal or broad range T cell epitope encoded on a plasmid of this invention binds six or more different class II MHC molecules.

Broad range antigenic helper T cell epitopes are known in the art. These include, for example, epitopes of tetanus toxoid (TT) and diphtheria toxoid (DT) (see, for example, Panina-Bordignon, P., et al., *Eur. J. Immunol.,* 19: 2237–2242 (1989) (characterization of universal tetanus toxoid helper T cell epitope peptides); Etlinger, H., *Immunol. Today,* 13: 52–55 (1992); Valmori, D., et al., *J. Immunol.,* 149: 717–721 (1992) (use of universal TT epitopes in candidate anti-malarial vaccine); Raju et al., *Eur. J Immunol.,* 25: 3207–3214 (1995) (broad range T cell epitopes of DT); Talwar, G. P., et al., *Proc. Natl. Acad. Sci. USA,* 91: 8532–8536 (1994) (use of TT and DT as universal epitopes in anti-human chorionic gonadotropin vaccine); Talwar, G. P., et al., *Proc. Natl. Acad Sci. USA,* 91: 8532–8536 (1994)).

In addition to TT and DT, other broad range or universal helper T cell epitope sequences useful in this invention include the universal class II MHC binding T cell epitopes: HA of influenza hemagglutinin, HBVnc, CS, and MT as described in Alexander et al. (*Cell,* 1: 751–761 (1994)). Still other T cell epitopes that may be encoded by the plasmids of this invention include those polypeptides derived from antigenic proteins derived from pertussis vaccine, Bacile Calmette-Guerin (BCG), polio vaccine, measles vaccine, mumps vaccine, rubella vaccine, and purified protein derivative (PPD) of tuberculin (see, for example, Etlinger, H., *Immunol. Today,* 13: 52–55 (1992)). Synthetic sequences, i.e., that are not derived from a naturally occurring organism, may also be used. Examples of synthetic broad range T cell epitopes are discussed in Alexander et al., *Immunity,* 1: 751–761 (1994).

Plasmids of this invention may encode a variety of non-endogenous CETP proteins, or fragments thereof, such as tetanus toxoid, particularly peptides of tetanus toxoid having amino acid sequences of amino acids 2–15 of SEQ ID NO:7 (a corresponding nucleotide coding sequence is nucleotides 13–54 of SEQ ID NO:5) and amino acid sequence of SEQ ID NO:10. Another source of universal or broad range T cell epitopes useful in the plasmids of this invention is diphtheria toxin, particularly peptides having amino acid sequences of amino acids 271–290, 321–340, 331–350, 351–370, 411–430, and 431–450 of SEQ ID NO:9. An example of corresponding nucleotide sequences encoding these broad range T cell epitopes from diphtheria toxin are nucleotides 811–870, 961–1020, 991–1050, 1051–1110, 1231–1290, and 1291–1350 of SEQ ID NO:8, respectively. Other sources of universal or broad range T cell epitopes that may be encoded on plasmids of this invention include, but are not limited to, class II MHC-associated invariant chain; hemagglutinin; keyhole limpet hemocyanin (KLH); a protein from known vaccines including pertussis vaccine, the Bacile Calmette-Guerin (BCG) tuberculosis vaccine, polio vaccine, measles vaccine, mumps vaccine, rubella vaccine, and purified protein derivative (PPD) of tuberculin; and also synthetic peptides as described by Alexander et al. (1994).

Furthermore, two or more copies of DNA coding for the same or various different universal helper T cell epitopes may be linked to one another to form multiple or multivalent helper T cell epitope portions of the vaccine peptides of this invention. For example, a plasmid of this invention may contain DNA segments encoding a multiple or multivalent helper T cell epitope portion having an amino acid sequence of a TT helper T cell epitope and a DT helper T cell epitope. The T cell epitope portion of the DNA vaccine may be continuous or may have intervening, in-frame segments encoding the B cell epitope portion or (preferably non-antigenic) segments linking the T and/or B cell epitopes.

A large number of possible T cell epitopes could be used as the T cell epitope portion of an immunogenic fusion polypeptide encoded on a plasmid of this invention. A routine methodology can be used to identify such additional broad range T cell epitopes which bind the antigen presenting sites of multiple class II MHC molecules (for example, Raju et al., *Eur. J. Immunol.*, 25: 3207–3214 (1995)). In this methodology, broad range T cell epitopes are identified by first obtaining peripheral blood from individuals that have recently been immunized with a protein of interest, i.e., the protein from which the T cell epitope is derived. Alternatively, peripheral blood from individuals not recently immunized can be used. However, T cells from such individuals need to be stimulated with the protein of interest in vitro to increase the number of T cells specific for the protein of interest. It is not necessary to know the identity of such a protein of interest to obtain a T cell epitope useful in this invention. It is sufficient if a protein can be isolated and purified, such as by extracting a band of the protein from a polyacrylamide gel after electrophoresis. Peptides of a protein of interest are made, for example, by limited proteolysis, or if the amino acid sequence of the protein is known, by synthesizing by standard methods overlapping polypeptides of at least five, and preferably approximately twenty, amino acids in length. A preferred group of individuals used as a source of peripheral blood for this methodology is a group of individuals who have recently been immunized with a known prophylactic vaccine, such as tetanus, diphtheria, or influenza vaccines, which contain one or more proteins that can be selected as the protein of interest to derive a useful T cell epitope. Each peptide from the protein of interest is individually co-cultured with peripheral blood lymphocytes purified from the peripheral blood of each individual from the group. The antigen presenting cells in each culture will bind certain peptides to their class II MHC molecules and display these on their cell surface. CD4+ T cells in the culture will bind a subset of these class II MHC bound peptides and consequently form the tertiary complex MHC:T cell epitope:T cell antigen receptor necessary to activate T cells and induce proliferation. Proliferation is detected by standard $^3$H-thymidine incorporation into DNA. Cultures showing proliferation by this assay indicate that the peptide co-cultured with the cells contained a helper T cell epitope. A peptide that stimulates proliferation of peripheral blood lymphocytes from multiple individuals is a candidate broad range T cell epitope useful in this invention. The amino acid sequence of such a peptide can be determined by standard amino acid sequence analysis. A DNA molecule encoding the peptide is prepared which encodes the peptide. If a DNA molecule encoding the peptide is not already available, a DNA sequence can be deduced using the genetic code and a DNA molecule having a nucleotide sequence encoding the peptide can be synthesized by standard DNA synthetic methods or obtained from a commercial vendor. The DNA molecule is then inserted in the same reading frame as the DNA sequence encoding the B cell epitope portion of the immunogenic fusion protein on a plasmid of this invention (see below).

B Cell Epitopes of CETP

The B cell epitope portion of the immunogenic fusion polypeptide encoded by the DNA plasmids of this invention comprises at least one B cell epitope of CETP, preferably the endogenous CETP of the vertebrate subject to be immunized. The use of at least two B cell epitopes is desirable and preferred because it increases the probability that the various autoantibodies produced in response to expression of the DNA vaccine in vivo will be able to bind to at least two distinct epitopes on each CETP molecule and thereby promote formation of immune complexes, which leads to efficient clearing of the CETP protein molecules from circulation.

B cell epitopes useful in this invention may be as small as 5 to 8 consecutive amino acid residues of the entire amino acid sequence of CETP. The DNA plasmids described herein contain a DNA sequence encoding a CETP B cell epitope portion of at least 15, and preferably 30–48 nucleotides in length. Preferred B cell epitopes of CETP for use in human vaccines will be encoded, individually, by at least a 15-nucleotide sequence of the coding sequence for CETP (see, for example, SEQ ID NO:1 encoding mature CETP (rabbit); SEQ ID NO:3 encoding mature CETP (human)), or degenerate sequences thereof encoding the same epitope. It should be noted that alleles of the rabbit CETP gene have been discovered and consequently, could be anticipated for the human gene (see, Nagashima et al, *J. Lipid Res.*, 29: 1643–1649 (1988); Kotake et al., *J. Lipid Res.*, 37: 599–605 (1996)). The B cell epitopes may be present in sequence or separated by intervening, in-frame segments encoding the T cell epitope(s) or (preferably non-antigenic) linking peptides of one or more amino acids. Of course, the actual length of the DNA sequence encoding the B cell epitope portion depends on the length of the particular B cell epitopes selected from CETP.

Although the DNA sequence encoding the B cell epitope portion of the immunogenic fusion polypeptide may encode two or more B cell epitopes of CETP, there are several reasons why the DNA sequence should not encode the entire amino acid sequence of the mature circulating CETP. For example, using less than the entire structural coding sequence for CETP limits the probability of producing antibodies that might cross-react with other self proteins. In addition, using less than the entire CETP structural coding sequence is one way to avoid producing potentially functional CETP protein or fragment, i.e., that would exhibit CE and/or TG transfer activity and thereby increase the overall CETP activity in the vaccinated individual. Using less than the entire CETP coding sequence also reduces the chance of eliciting cell-mediated autoimmune responses. Whether a region of CETP or even a particular CETP B cell epitope also includes a T cell epitope can be readily determined by testing the B cell epitope or region of CETP in a cytotoxic T cell or proliferation assay (see, for example, *Current Protocols in Immunology,* (Coligan et al., eds.) (John Wiley & Sons, New York, 1994) pp. 3.11.4–3.11.7 and 3.12.9–3.12.14).

The carboxyl terminal 26 amino acids of human CETP is involved in neutral lipid transfer activity (Swenson et al., *J. Biol. Chem.,* 264: 14318–14326 (1989)). In particular, a 13-amino acid sequence (Phe-463 to Leu-475 in human CETP, SEQ ID NO: 4; amino acids Phe-483 to Leu-495 in rabbit CETP, SEQ ID NO:2) and also possibly Asp-460 (human) (Asp-480, rabbit) are particularly important for neutral lipid binding and transfer activity (Wang et al., *J. Biol. Chem.,* 268: 1955–1959 (268); Wang et al., *J. Biol. Chem.,* 267: 17487–17490 (1992)). This region has already been shown to be immunogenic as a B cell epitope of CETP, and a monoclonal antibody (TP2) directed at this region has been shown to inhibit neutral lipid transfer. Accordingly, in a preferred embodiment, a plasmid used as a DNA vaccine useful in humans comprises a DNA sequence encoding the CETP B cell epitope as defined by the amino acid sequence of Phe-461 to Ser-476 or Phe-463 to Leu-475 of mature human CETP (see SEQ ID NO: 4).

A DNA sequence encoding a second B cell epitope of CETP is defined by the amino acid sequence of Leu-349 to Ile-367 of human CETP (SEQ ID NO: 4) (corresponding rabbit amino acid sequence Arg-350 to Ile-368 of SEQ ID NO: 2). In preferred embodiments this DNA encoding this epitope is included in the structural coding sequence of the immunogenic polypeptide to produce a second antibody species, specific for a second CETP epitope, in vivo. Antibodies to a second epitope would allow the formation of immune complexes involving CETP, and consequently promote the removal (clearance) of the complexed CETP. This peptide was selected for its potential antigenicity and high possibility for surface expression on native CETP.

Other suitable B cell epitopes of CETP could be selected, for example, based on previously defined antibody binding sites (see, for example, Roy et al., *Lipid Res.,* 37: 22–34 (1996)) or by analysis of the amino acid sequence for structural motifs associated with a propensity for antibody recognition.

Transcription and Replication Control Sequences

The DNA plasmids of this invention must contain the DNA sequences necessary to permit a sufficient level of in vivo expression of the encoded immunogenic fusion polypeptide to elicit production of autoantibodies reactive with endogenous CETP. Thus, the DNA plasmid according to the present invention comprises: the structural coding sequence for an immunogenic fusion polypeptide comprising a DNA sequence coding for at least one T cell epitope and a DNA sequence coding for at least one B cell epitope of CETP as described above, and a promoter sequence or a promoter/enhancer sequence to direct transcription of the structural coding sequence for the immunogenic fusion polypeptide. In some instances it may be desirable, as described above, to include coding sequences for one or more additional amino acids, for example, to space the epitope portions, to disrupt unintentionally created neo-epitopes formed by the juxtaposition of the selected T and/or B cell epitopes, to insert proteolytic cleavage sites, etc. It may also be desirable to include a bacterial origin of replication and a selectable marker(s), for example, to aid in production of large quantities of the plasmid vaccine in bacterial culture.

Transcription of the immunogenic fusion protein structural coding sequence is under the control of a promoter sequence and an enhancer sequence. A variety of promoter and enhancer sequences are known and may be evaluated for this purpose in accordance with Example 1, below. Promoter/enhancer sequences that may be used in plasmids of this invention include, but are not limited to, CMV promoter/enhancer sequence, adenovirus promoter/enhancer sequence, and β-actin promoter/enhancer sequence in a preferred embodiment, the promoter and enhancer sequences are the CMV immediate-early promoter/enhancer sequence. Whether a particular promoter/enhancer is more or less useful than another promoter/enhancer sequence in the plasmids of this invention can be determined by comparing the ability of promoter/enhancer evaluated by testing whether the promoter/enhancer permits expression of a standard reporter gene, such as luciferase or β-galactosidase, and the production of antibody reactive with the expressed reporter in an animal model for gene expression, such as in rabbits or mice. Generally the higher the level of expression of the reporter gene product and/or the higher the level of production of antibodies reactive with the expressed reporter gene product, the more useful that particular promoter/enhancer will be at directing transcription of the structural coding sequence for the immunogenic fusion protein in the plasmids used as DNA vaccines.

Methods of Administering DNA Vaccine

The plasmid-based vaccines according to the invention may be administered in any conventional manner. Suitable methods include, for instance, direct administration of plasmid DNA via intramuscular injection, intradermal injection or DNA-coated microprojectiles. The amount of vaccine administered will vary widely according to the method of administration, the tissue (for example, skeletal muscle, skin) into which the vaccine is administered, the desired titer of anti-CETP antibodies, the particular therapeutic needs of the subject to be immunized, etc. Very large amounts of DNA vaccine, on the order of 10 mg/kg of body weight, may be administered with injection into muscle tissue, whereas for coated microprojectiles very much less vaccine may possibly be used. The dosage of vaccine and immunization protocol should be calibrated to obtain a beneficial response, which can be measured in a variety of ways, depending on the clinical setting, for example, by measuring change in lipoprotein profile (for example, increased HDL/LDL ratio), anti-CETP antibody titer, serum CETP concentration, change in CETP activity, etc.

The following examples are provided in order to illustrate the invention described herein. These examples are not intended to in any way limit the scope of the invention.

EXAMPLE I
Selection of the Optimal Promoter/Enhancer and Derivation of the pCMV-LUC Plasmid This experiment was designed to evaluate the effectiveness of several promoter/enhancers to express a reporter gene (luciferase) and elicit immune responses, to select the best one for use in future vaccination experiments.

Three different plasmids were constructed, with the firefly luciferase gene expressed under the control of the β-actin, the adenovirus, or the human cytomegalovirus (CMV) immediate early promoter/enhancer. Since the CMV construct (pCMV-LUC) was used in further experiments, details of its construction are as follows.

The CMV promoter/enhancer, with the pUC19 plasmid vector backbone containing the ampicillin resistance gene (amp$^r$), was excised by digestion with BamHI from the plasmid pCMVβ (Clontech Laboratories, Palo Alto, Calif.). The luciferase gene (LUC), with adjacent splice donor/acceptor sites and polyadenylation signal derived from SV40, was generated from the pGL2-Promoter Vector (Promega Corp., Madison, Wis.) on a BamHI fragment, as follows: pGL2 was digested with HindIII and ends were filled in with Klenow polymerase. BamHI linkers were attached and digested with BamHI. This LUC fragment was gel purified and ligated to the CMV+ vector fragment from pCMVβ. The structure of the resulting plasmid, pCMV-LUC, was confirmed by restriction mapping. See FIG. 1.

Luciferase expression was confirmed by assaying luciferase activity in lysates of COS cells transfected with all 3 constructs.

Four groups of nine mice were established. Three of the groups were injected intramuscularly, in both quadriceps, with 50 µg/quadriceps of one of the three constructs (above) in 25 µl phosphate buffered saline (PBS). The fourth group of mice served as a control and received two 25 µl injections of PBS only. The animals received an equal boost of the same plasmid (or PBS control) after 4 weeks and were bled at approximately 2-week intervals. One mouse from each group was sacrificed at day 2 and at day 32 (48 hours after injections) in order to assay tissue for luciferase production. At the conclusion of the experiment the animals were euthanized with $CO_2$ and the injected muscle tissue was assayed for luciferase production.

Figure 2:
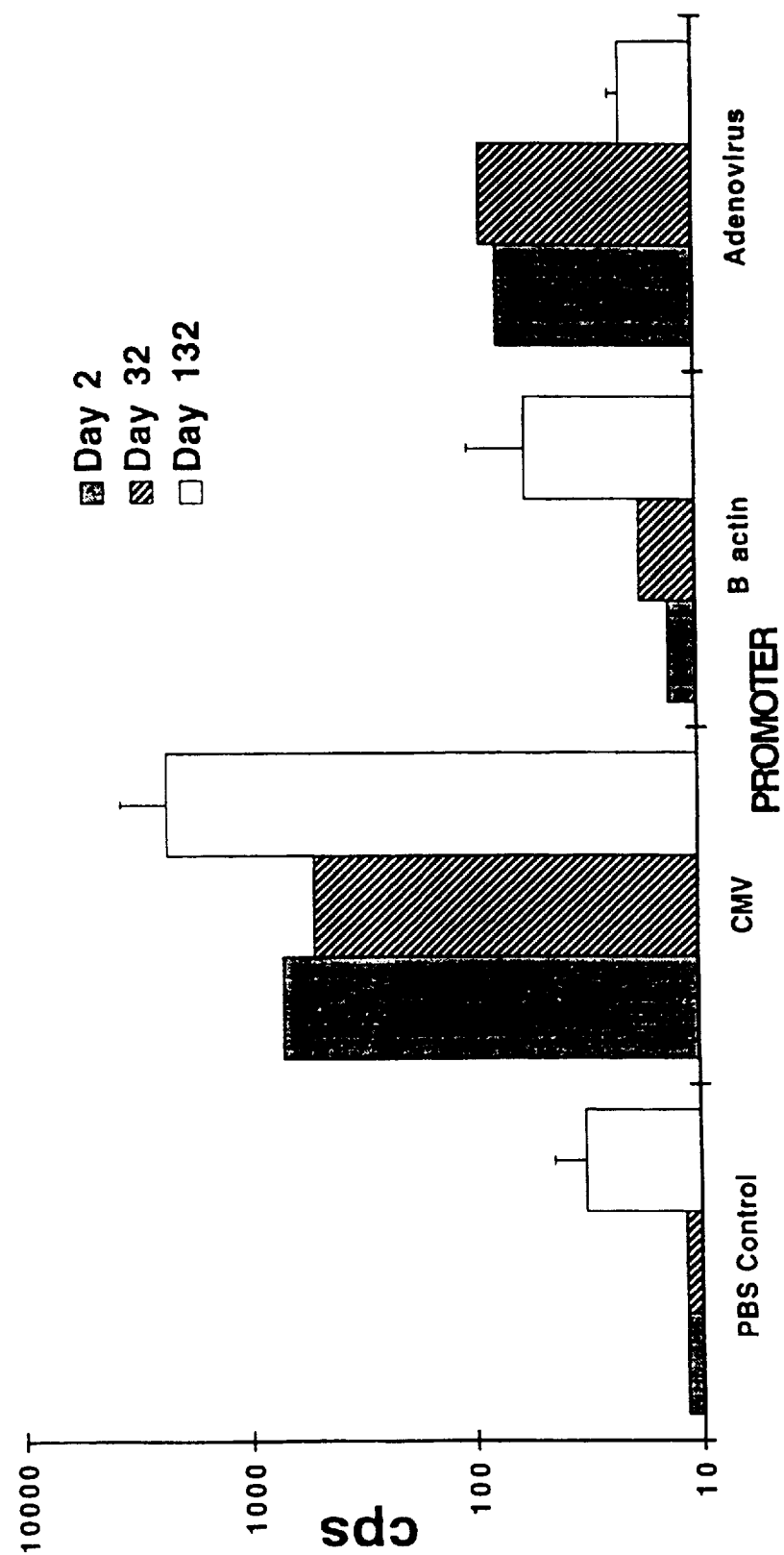
FIG. 2 is a bar graph showing luciferase activity measured at different time points in homogenates of quadriceps from mice injected intramuscularly with plasmid constructs having the luciferase gene under the transcriptional control of three different promoters: CMV, β-actin, and adenovirus. Homogenates were prepared from quadriceps from mice on Day 2, 32, or 132 after being injected with one of the plasmid constructs. "PBS Control" refers to homogenates prepared from control mice on Day 2, 32, or 132 after being injected with sterile phosphate buffered saline (PBS).

Quadriceps tissue samples were prepared by mechanical homogenization of the muscle with 400 µl reporter lysis buffer (Promega Corp., Madison, Wis.). The homogenate was vortexed and centrifuged at high speed and the supernatant removed. One hundred µl of beetle luciferin (Promega Corp.) was added to 20 µl of the supernatant. The light emitted due to the enzyme-substrate interaction was measured for 5 seconds in a Packard Top Count scintillation counter. Active luciferase enzyme was detected in tissue samples from animals injected with all three of the plasmids. However, the animals injected with pCMV-LUC had the highest level of active enzyme production (see, FIG. 2), and this promoter/enhancer was selected for use in further experiments. The values for days 2 and 32 involved one animal only. On day 132, when the remaining animals were sacrificed and the quadriceps muscles were assayed, significant active luciferase was detected in the CMV group at levels as high as or higher than that detected on days 2 and 32. It is particularly striking that active luciferase was found in muscle tissue 132 days after the last injection of pCMV-LUC. The longevity of the expression of protein with the pCMV-LUC construct was important to the logic of using the CMV promoter/enhancer for the CETP vaccine plasmids described below.

Figure 3:
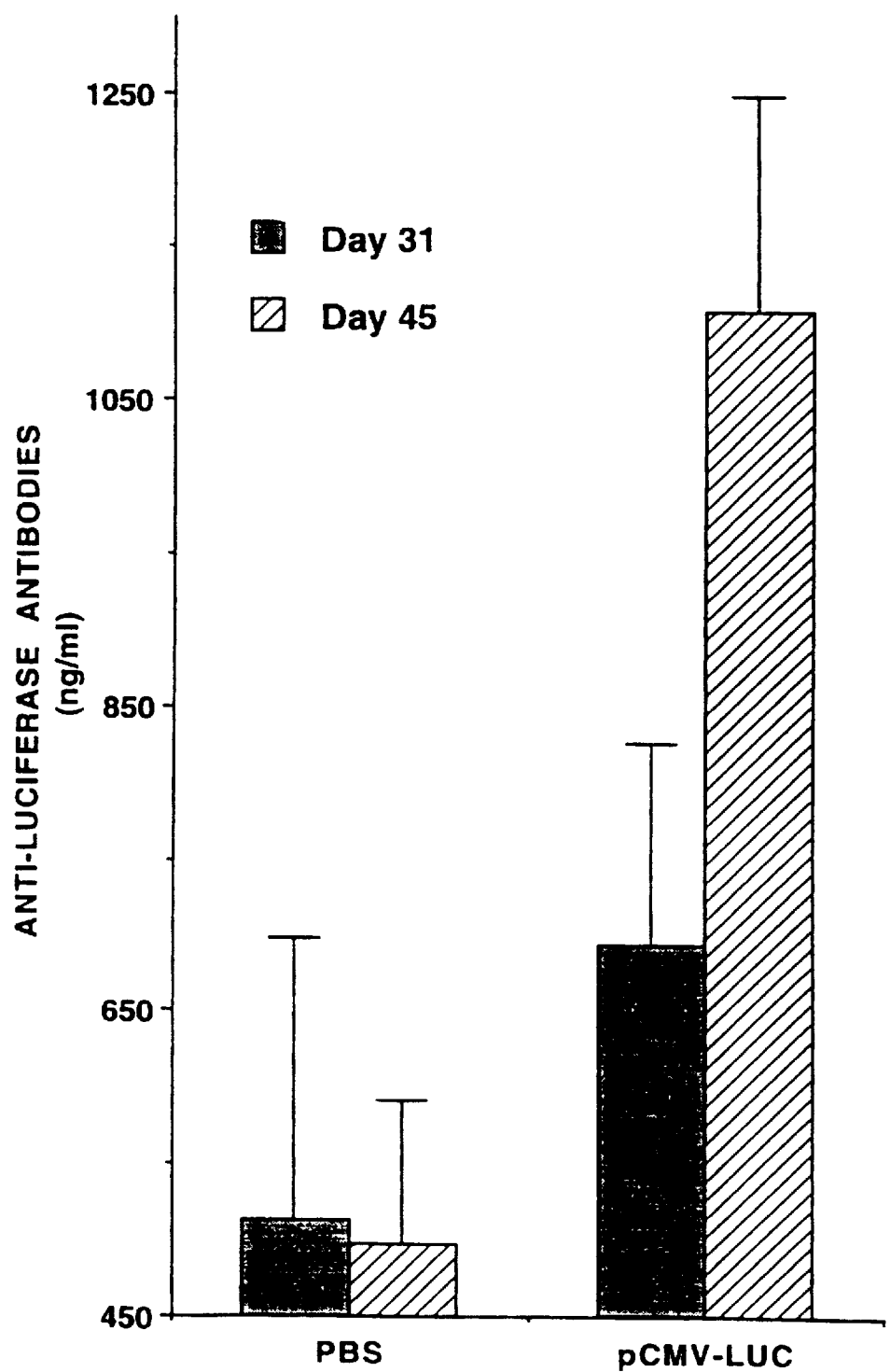
FIG. 3 is a bar graph showing anti-luciferase antibody production in mice injected intramuscularly with the plasmid pCMV-LUC, in plasma blood samples obtained from mice at 31 and 45 days after immunization.

Antibodies to luciferase were detected in bleeds taken on day 31 and 45. The ELISA was performed as follows: Biotinylated luciferase was adhered to a streptavidin-coated plate for 1 hour, then washed with PBS containing 0.05% Tween 20. Mouse plasma was diluted in PBS with 1% BSA in PBS, incubated in the plate for approximately two hours, then washed. Goat-anti-mouse-HRP (goat anti-mouse antibody conjugated to horseradish peroxidase) was added and incubated for 45 minutes. After incubation for 2 hour at 20° C. on a rotating shaker, and washing, the reaction was developed with 3,3',5,5'-tetramethylbenzidine (TMB, Kirkegaard & Perry Laboratories, Inc., Gaithersburg, Md.), stopped with 2N $H_2SO_4$, and read at 450 nm. Antibodies to luciferase were detected in bleeds taken on day 31 and 45. The results are presented graphically in FIG. 3.

A significant increase in antibody production was seen subsequent to the second injection of plasmid. This experiment indicates that luciferase produced by a plasmid-based vaccine can elicit antigen-specific antibodies. These experiments indicated that the CMV promoter/enhancer is effective at driving the expression of an immunogenic protein in vivo.

EXAMPLE II pCMV-CETP/TT Plasmid Vaccine Design and Construction

The rabbit CETP fragment corresponding to the C-terminal amino acids 481–496 (see, SEQ ID NO: 2) has been identified to contain the functional, neutral lipid binding site of rabbit CETP. This fragment includes the epitope recognized by TP2, an anti-CETP monoclonal antibody that inhibits CETP activity (Swenson, T. L., et al., *J. Biol. Chem.*, 264: 14318–14326 (1989)). A second epitope of rabbit CETP (amino acids 350–368 of SEQ ID NO:2) was selected for the plasmid-based vaccine to elicit antibodies to a second epitope which would allow the formation of immune complexes involving CETP, and consequently promote the clearance of the immune complexed CETP. This epitope was selected for its potential antigenicity and high possibility for surface expression on native CETP.

A tetanus toxoid sequence recognized as almost universally antigenic (Panina-Bordignon, P., et al., *Eur. J. Immunol.*, 1989: 2237–2242 (1989)) was selected as the T cell epitope portion. This TT epitope has been used successfully in generating an autoimmune antibody response to hCG (Talwar, G. P., et al., *Proc. Natl. Acad. Sci.*, 91: 8532–8536 (1994)). It would be expected to be particularly effective also in vaccines administered to subjects previously vaccinated with tetanus toxoid.

Figure 4:
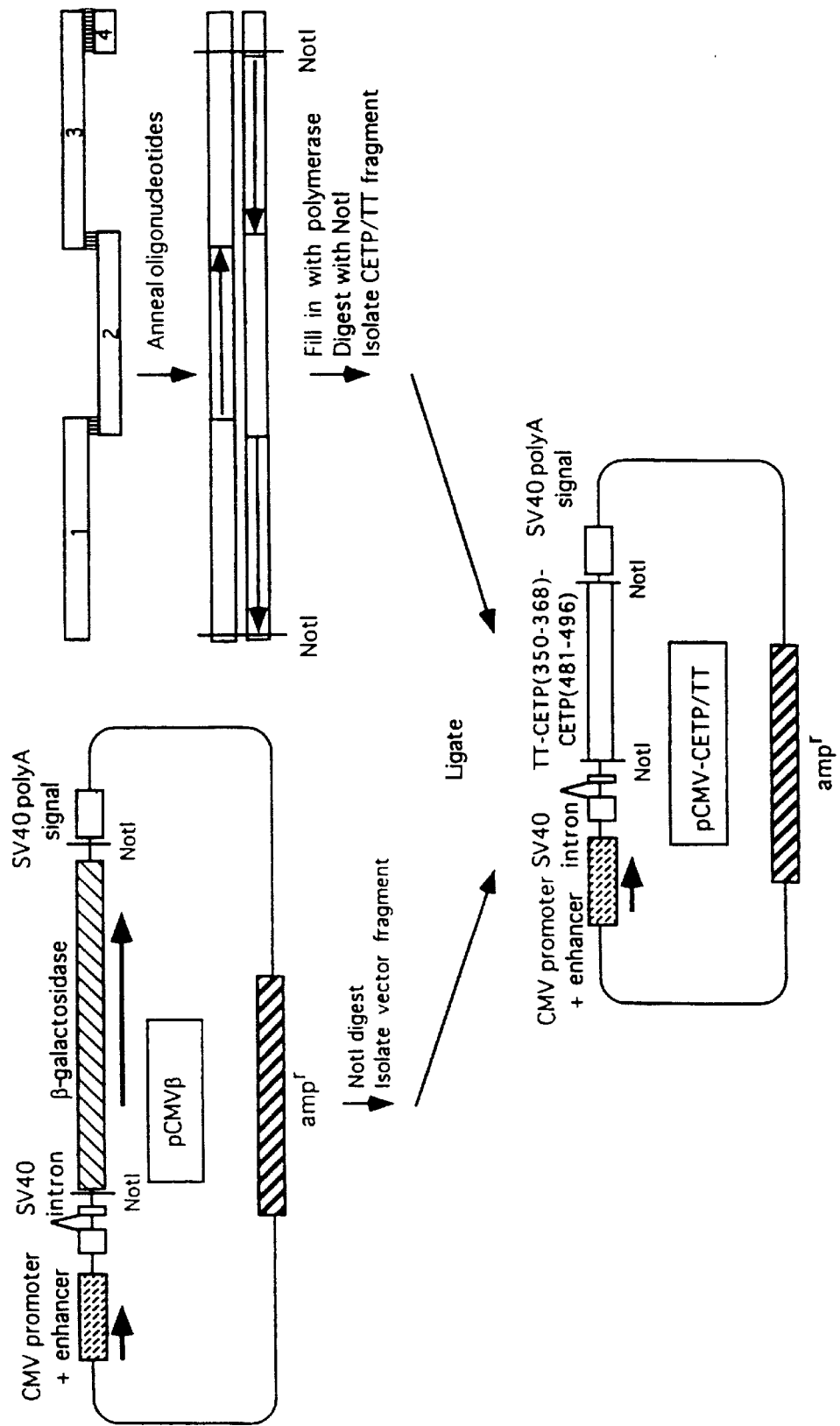
FIG. 4 is a diagram showing the construction of plasmid-based vaccine pCMV-CETP/TT.

A set of four oligonucleotides were synthesized which encode the TT and CETP epitopes as well as an initiating methionine residue, a 5' Kozak sequence (for efficient translation), a stop codon, and flanking NotI sites for cloning. The oligonucleotides were annealed and extended with DNA polymerase. See FIG. 4.

The double-stranded product was digested with NotI and gel purified to isolate the CETP/TT insert below:

```
GCGGCCGCCATG CAG TAC ATC AAG GCC AAC TCC AAG TTC ATC GGC ATC ACG GAG
CGCCGGCGC TAC GTC ATG TAG TTC CGG TTG AGG TTC AAG TAG CCG TAG TGC CTC
   NotI    M   Q   Y   I   K   A   N   S   K   F   I   G   I   T   E
          |<                  TETANUS TOXOID                       >|

CGC TTC CCC CGC CCA GAT GGC CGA GAA GCT GTG GCC TAC AGG TTT GAG GAG GAT ATC
GCG AAG GGG GCG GGT CTA CCG GCT CTT CGA CAC CGG ATG TCC AAA CTC CTC CTA TAG
 R   F   P   R   P   D   G   R   E   A   V   A   Y   R   F   E   E   D   I
|<                        rabbit CETP (350-368)                          >|

TTC GGT TTT CCC AAG CAC CTG CTG GTG GAT TTC CTG CAG AGC CTG AGC TAGCGGCCGC
AAG CCA AAA GGG TTC GTG GAC GAC CAC CTA AAG GAC GTC TCG GAC TCG ATC GCCGGCG
```

```
                                -continued
F  G  F  P  K  H  L  L  V  D  F  L  Q  S  L  S  *
|<                   rabbit CETP (481-496)         >| STOP  NotI
```

In the above insert, the coding strand is SEQ ID NO: 5, the antisense strand is SEQ ID NO: 6, the amino acid sequence is SEQ ID NO: 7. The insert is also depicted in FIG. 5.

The plasmid pCMVβ (Clontech Laboratories) was digested with NotI to generate a fragment containing the CMV promoter/enhancer on a pUC19 backbone, with the ampicillin resistance gene (amp$^r$). This fragment also includes splice donor/acceptor sites and a polyadenylation signal derived from SV40, flanking the NotI insertion site. The synthesized CETP/TT insert was ligated to the CMV+ vector fragment from pCMVβ. Plasmids were recovered by bacterial transformation and inserts confirmed by DNA sequencing.

EXAMPLE III
Vaccination of Rabbits With the pCMV-LUC and pCMV-CETP/TT Plasmids

An experiment employing a rabbit model for atherosclerosis (Daley et al., *Arterioscl. Thromb.*, 14: 95–104 (1994)) was designed to test whether a DNA plasmid-based vaccine according to this invention would break tolerance to endogenous CETP resulting in production of antibodies reactive with endogenous CETP and/or inhibition in the development of atherosclerotic lesions in the rabbit aorta. New Zealand white rabbits (n=8) were immunized with both plasmids pCMV-LUC and pCMV-CETP/TT and monitored for production of anti-luciferase and anti-CETP antibody production as well as for the ability to inhibit progression of atherosclerosis when placed on atherogenic diets, i.e., diets supplemented with amounts of cholesterol known to generate definite and extensive atherosclerotic lesions in control rabbits (Daley et al., id.). The daily protocol for this experiment employing 13 rabbits is shown in FIG. 6.

Eight rabbits (rabbits #1–#8) were vaccinated in three sites intramuscularly in each quadriceps with a vaccine preparation consisting of an equal mixture of the plasmids pCMV-CETP/TT and pCMV-LUC on Day 0. pCMV-LUC served as a reporter plasmid to allow an additional level of experimental quantitation of plasmid-dependent protein expression and of antibody production to the plasmid-encoded, expressed protein. Specifically, blood samples (for example, 3–5 ml from an ear vein) were taken from the rabbits once a week for 3 weeks to establish various pre-vaccination values ("prebleeds" designated PRE 1, PRE 2, and PRE 3 in FIG. 6). Blood samples, taken after an overnight fast (about 16 hours), were collected into EDTA anti-coagulant. Following the last prebleed (PRE 3), each animal was vaccinated with three injections into each quadriceps. Each of these 6 injections consisted of 50 μg of the pCMV-LUC plasmid and 50 μg of the pCMV-CETP/TT plasmid in 100 μl of PBS containing a small amount of carbon powder (to aid in excising the injection site). Forty-eight hours after the vaccination one rabbit (rabbit #8) was sacrificed, and its blood and quadriceps were removed for analysis. All animals were bled and boosted (as above, except that blue dye was used instead of carbon) four weeks (Day 28) after the primary vaccination. Again, 48 hours after the boost vaccination, one rabbit (rabbit #7) was sacrificed, and its blood and quadriceps were removed.

Figure 7:
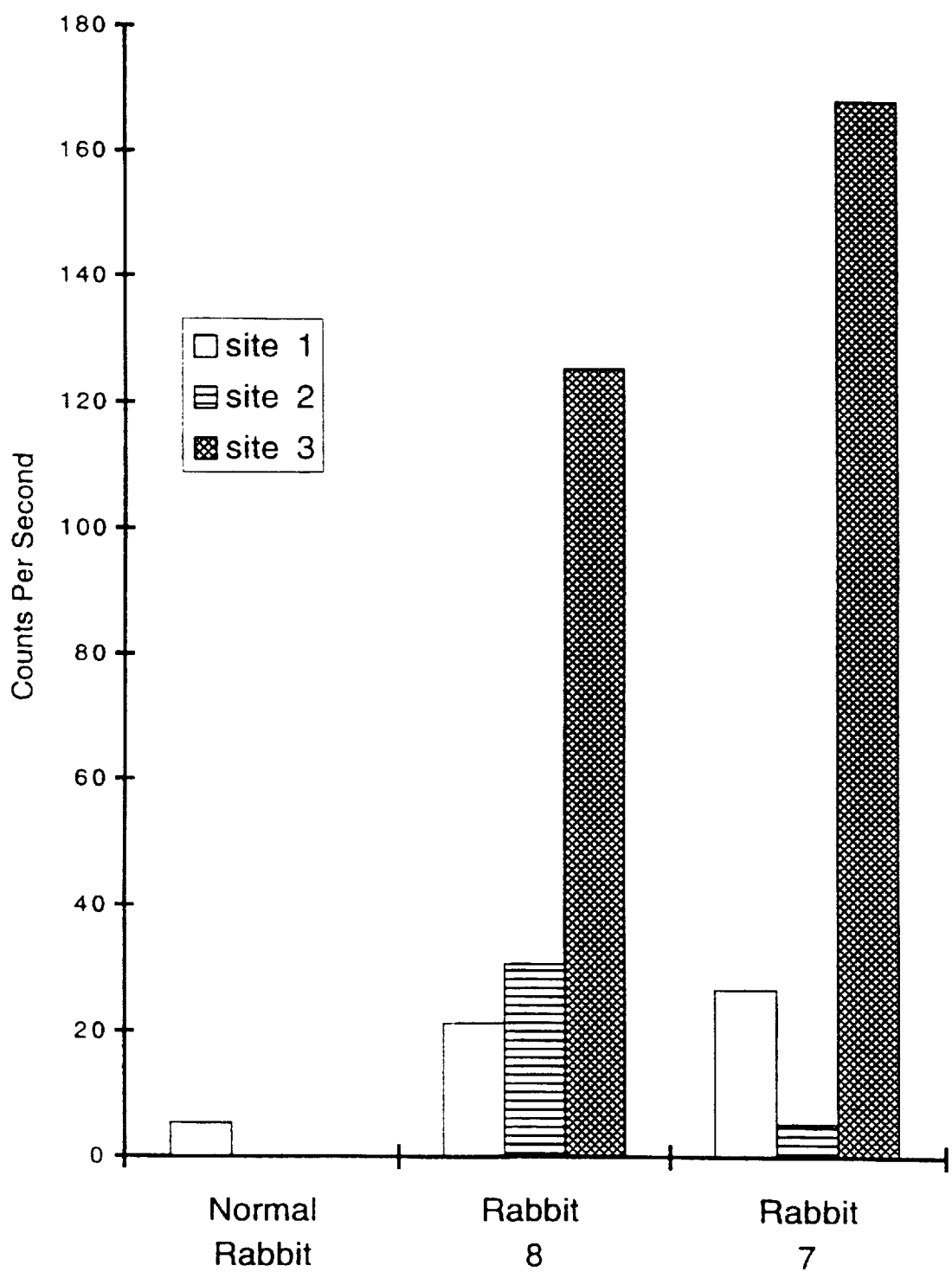
FIG. 7 is a histogram showing luciferase expression in tissue homogenates taken from the approximate areas of each of three sites in rabbit quadriceps which were injected with both pCMV-LUC and pCMV-CETP/TT plasmids. Luciferase activity is expressed in counts per second. "Normal Rabbit" refers to luciferase activity in tissue homogenate taken from a normal control rabbit that did not receive either plasmid. "Rabbit 8" refers to tissue homogenates prepared from approximate sites of injection of plasmids pCMV-LUC and pCMV-CETP/TT into quadriceps of rabbit #8 which was sacrificed 48 hours after being injected with plasmids on Day 0. "Rabbit 7" refers to tissue homogenates prepared from approximate sites of injection of pCMV-LUC and pCMV-CETP/TT into quadriceps of rabbit #7 which was sacrificed 48 hours after receiving a second injection (boost) of plasmids pCMV-LUC and pCMV-CETP/TT on Day 28.

The tissue samples around the areas of carbon marks in the quadriceps of rabbits #8 and #7, respectively, were taken and tissue homogenates prepared. Using the luciferase assay described above, luciferase enzymatic activity was detected in tissue taken from the primary (Day 0) injection sites as shown in FIG. 7. For example, unvaccinated muscle tissue gave a background signal of approximately 5.33 counts per second (cps) in this assay (Normal Rabbit in FIG. 7). Muscle tissue from a vaccinated site of rabbit #8 (site 3 for Rabbit 8 in FIG. 7), removed 2 days after vaccination, gave a luciferase signal of 125 cps (23.5 times background), and muscle tissue from vaccinated sites of rabbit #7, removed 30 days after vaccination showed a luciferase signal of 26.7 cps (site 1 for Rabbit 7 in FIG. 7, 5 times background) and 168 cps (site 3 for Rabbit 7 in FIG. 7, 31.5 times background). The fact that not all tissue samples showed luciferase activity was probably due to the difficulty in locating precisely the sites of deposition of plasmid despite the use of carbon to mark the vaccination sites. However, the data from samples from site 3 of rabbits #8 and #7 shown in FIG. 7 clearly demonstrate that this plasmid construct is effective as a vaccine vector (regardless of insert) in rabbits.

Two additional blood samples (BLEEDS 3 and 4 on Days 44 and 57, respectively, in FIG. 6) were taken at two-week intervals. The animals were then vaccinated three times intramuscularly with 0.5 ml of an alum-adsorbed preparation of tetanus toxoid (Connaught Laboratories, Inc., Swiftwater, Pa.) on Days 66, 91, and 128 (see FIG. 6). This was done to determine if tetanus vaccination would increase the CETP vaccine efficacy and to better mimic the human situation.

Initially, all rabbits in this experiment were fed standard rabbit chow. In order to induce the formation of atherosclerotic-like lesions, rabbits were placed on a diet containing either 0.25% (w/w) cholesterol or 0.5% (w/w) cholesterol at Days 99, 112, and 154, as indicated in FIG. 6. Additional blood samples (BLEEDS 8–12) were taken, and the entire experiment terminated by Day 220.

An ELISA designed to detect free serum antibodies recognizing a rabbit CETP peptide having an amino acid sequence corresponding to amino acids 477–496 of rabbit CETP (amino acids 477–496 of SEQ ID NO:2) was performed essentially as follows: Wells of a 96-well streptavidin-coated plate were coated with the CETP 477–496 biotinylated peptide by incubation of 100 μl of a solution of the peptide (1.0 μg/ml PBS) for 30 minutes to 1 hour, then washed with 2× PBS containing 0.1% Tween 20. Immunized rabbit plasma (or normal rabbit plasma; NRP) was diluted in PBS with 1% bovine serum albumin (BSA), incubated in the plate for approximately two hours, then washed. Goat-anti-rabbit-HRP (goat anti-rabbit antibody conjugated to horseradish peroxidase) was added and incubated for approximately 45 min. on a rotating shaker. Following washing, the reaction was developed with 3,3',5,5'-tetramethylbenzidine (TMB, Kirkegaard & Perry Laboratories, Inc., Gaithersburg, Md.), stopped with 2N $H_2SO_4$, and read at 450 nm spectrophotometrically using an ELISA plate reader.

Figure 8:
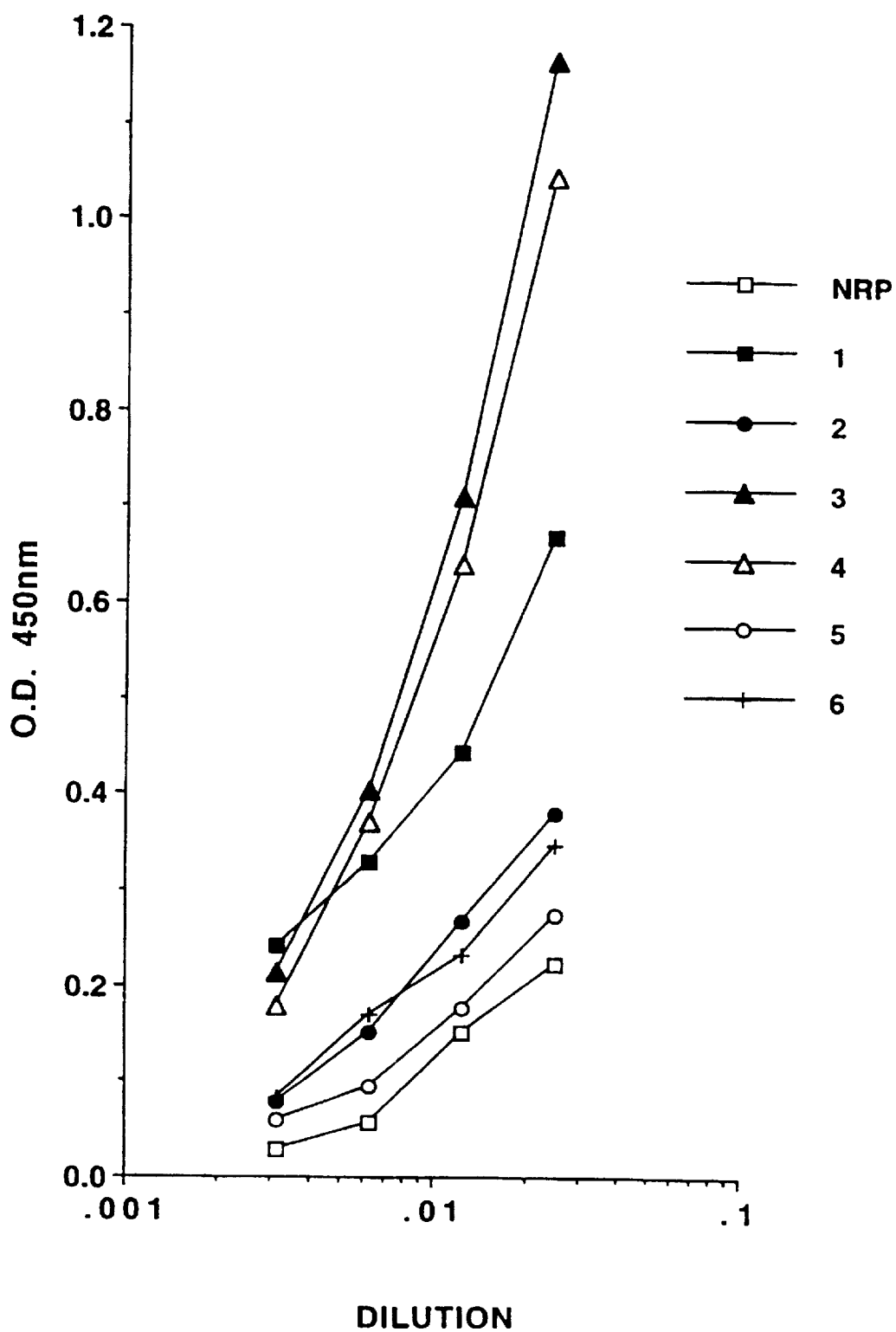
FIG. 8 is a graph showing detection by ELISA of anti-rabbit $CETP_{477-496}$ antibodies in plasma taken on Day 57 from six rabbits (rabbits #1–#6) vaccinated with plasmid pCMV-CETP/TT. Plasma was assayed from rabbit #1 (filled square), rabbit #2 (filled circle), rabbit #3 (filled triangle), rabbit #4 (open triangle), rabbit #5 (open circle), and rabbit #6 (cross). "NRP" refers to plasma taken from a control rabbit that was not injected with either plasmid pCMV-LUC or plasmid pCMV-CETP/TT (open square).

Plasma samples from the six rabbits (rabbits #1–#6), taken 57 days after the primary vaccination were diluted and assayed for production of antibody reactive with the rabbit $CETP_{477-496}$ peptide. Plasma from an uninjected rabbit (NRP) was also assayed. The results are depicted in FIG. 8, indicating a range in the levels of production of anti-rabbit CETP 477–496 peptide antibody in vaccinated animals by Day 57.

Plasma samples from rabbits #2, #3, #5, and #6 were also taken on Day 220 and assayed to determine whether rabbits vaccinated with pCMV-CETP/TT continued to produce detectable levels of antibody to CETP as determined by an ELISA using the rabbit CETP 477–496 peptide. Wells of a 96-well streptavidin-coated plate were coated with biotinylated $CETP_{477-496}$ peptide by incubation of 100 μl of a solution of the peptide (200 ng/ml in PBS) for 1 hour. Non-specific binding was prevented by incubating with Blocking Buffer (PBS with 1% (w/v) BSA, 1% (w/v) non-fat dry milk, 0.5% (w/v) gelatin, 0.9% (v/v) Triton X-100, and 0.6% (v/v) NP-40) overnight at 4° C. on rotating shaker at 150 rpm, followed by washing three times with Wash Buffer (2× PBS with 0.05% (v/v) Tween 20). Immunized rabbit plasma (or normal rabbit plasma, NRP) was diluted in Blocking Buffer, incubated in the plate for approximately two hours, then washed. Goat-anti-rabbit-HRP was added and incubated for approximately 1 hour on a rotating shaker. Following washing, the reaction was developed with TMB, stopped with 50 μl 2N $H_2SO_4$, and read at 450 nm on an ELISA plate reader. Data from the plasma of the four vaccinated rabbits taken on Day 220 and normal rabbit plasma (NRP) are shown in FIG. 9.

Figure 9:
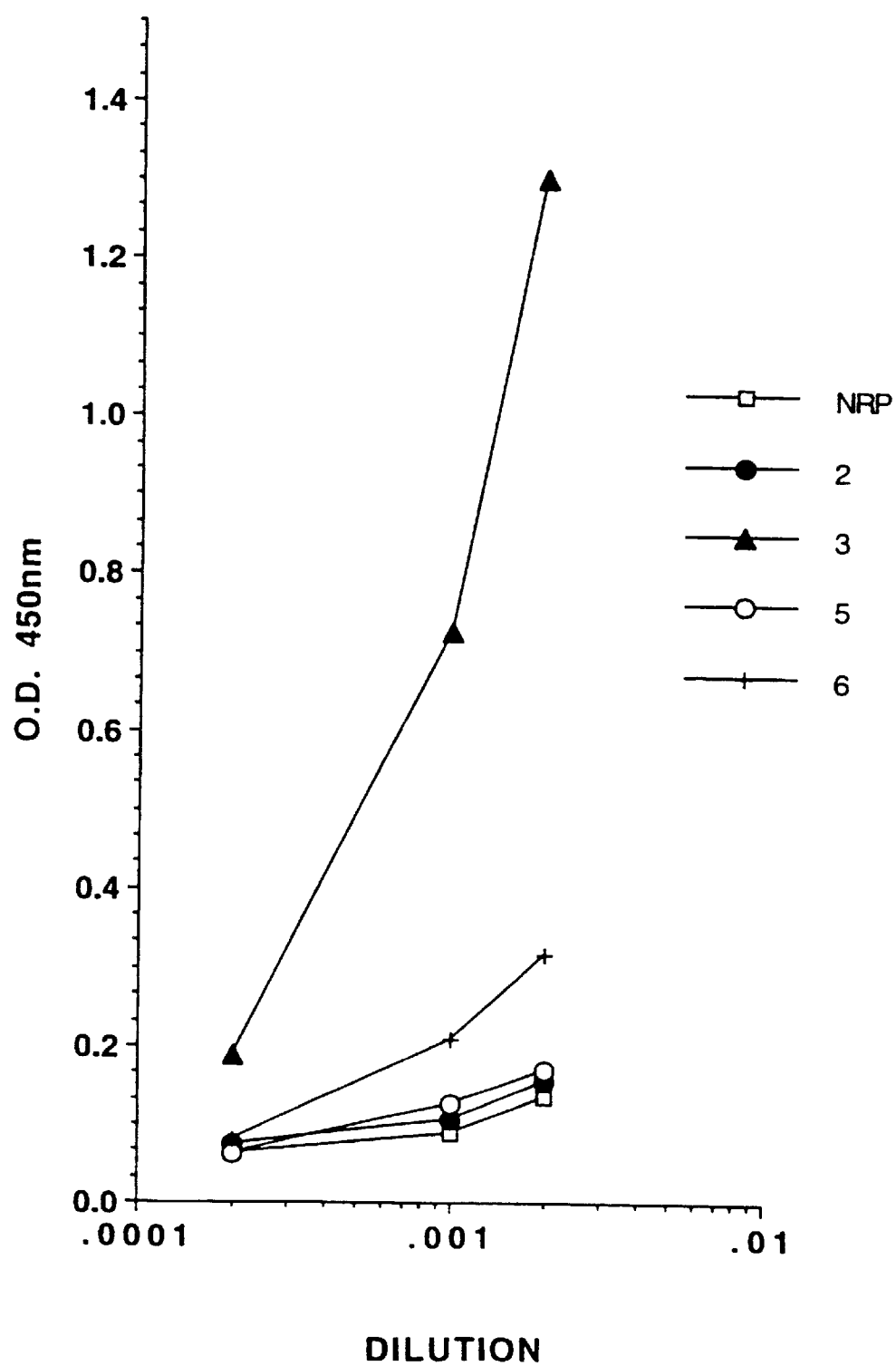
FIG. 9 is a graph showing detection of anti-rabbit $CETP_{477-964}$ antibodies in plasma taken at Day 220 from four rabbits vaccinated with plasmid pCMV-CETP/TT. Plasma was assayed from rabbit #2 (filled circle), rabbit #3 (filled triangle), rabbit #5 (open circle), and rabbit #6 (cross). "NRP" refers to plasma taken from a control rabbit that was not injected with plasmids pCMV-LUC and pCMV-CETP/TT (open square).

The data in FIG. 9 indicate that plasma from rabbit #3 clearly contained detectable antibody to the rabbit CETP 477–496 peptide according to this ELISA. Using this ELISA, plasma from rabbit #6 also appeared to contain some detectable anti-CETP antibody. However, while the signal from the plasma of rabbit #3 was substantial, the signal from the plasma of rabbit #6 was near baseline (see, for example, FIG. 9). This signal is interpreted as indicating the presence of antibodies in rabbit #3 and probably rabbit #6 recognizing this epitope of CETP.

The plasma samples were assayed in another ELISA designed to quantitate antibody to the $CETP_{477-496}$ peptide. Wells of a 96-well streptavidin-coated plate were coated with biotinylated $CETP_{477-496}$ peptide by incubation of 100 μl of a solution of the peptide (1 μg/ml in PBS) for 30 minutes to overnight, then washed with PBS containing 0.05% (v/v) Tween 20. Non-specific binding was prevented by incubating with Blocking Buffer (described above) for two hours at room temperature on a rotating shaker at 150 rpm, followed by washing four times with Wash Buffer (described above). Immunized rabbit plasma was diluted in Blocking Buffer, incubated in the plate for 1.5 hours, then washed. Goat-anti-rabbit-HRP was added and incubated for approximately 1 hour on a rotating shaker. Following washing, the reaction was developed with 100 μl of TMB, stopped with 50 μl of 2N $H_2SO_4$, and read at 450 nm in an ELISA plate reader. The concentration of the specific antibodies was estimated using a standard curve made from biotinylated rabbit immunoglobulin at 15 to 250 ng/ml.

The results of this assay are shown in FIG. 10. Again, the plasma sample of rabbit #3 clearly contained detectable antibody reactive with the rabbit $CETP_{477-496}$ peptide. However, this assay did not detect antibody reactive with the peptide in plasma samples of rabbits #2, #5, and #6. Unimmunized rabbits #10, #12, and #13 exhibited a background signal in this assay similar to rabbit #2. The plasma sample of rabbit #4 also appeared to contain detectable antibody to CETP according to this assay. However, rabbit #4 was terminated according to the protocol at day 148 (see FIG. 6), whereas rabbits #2, #3, #5, and #6 were alive throughout the entire 220 days of the experiment.

The observation that there was inter-animal variation in the response to the vaccine is consistent with the literature on plasmid-based vaccines. It can consequently be deduced that the plasmid-based vaccine produced the desired protein in a humorally immunogenic form. It is important to note that this assay detects only free antibody in the plasma samples. Anti-CETP antibodies bound to endogenous CETP (presumably the majority) would not be detected. Also, these rabbits had not been previously vaccinated with tetanus vaccine. It is likely that titers would be raised in a subject receiving or having previously received tetanus vaccine, such as is the case for many adult humans who have received vaccinations against tetanus.

As indicated in the daily protocol in FIG. 6, rabbits #2, #3, #5 and #6 in this experiment were switched from a diet of basic rabbit chow to diets supplemented with various amounts of cholesterol known to produce atherosclerotic-like lesions in rabbits (Daley et al., *Arterioscler. Thromb.*, 14: 95–104 (1994)) on Days 99, 112, and 154. To determine whether the plasmid-based vaccine may affect the development of atherosclerosis, the aortas of these rabbits were examined histologically for the development of atherosclerotic lesions. After blood samples were taken on Day 220, rabbits #2, #3, #5, and #6 were sacrificed. The entire aortas from each of the four rabbits were removed and placed into fixative solution (3.7% v/v formaldehyde). Loose tissue, adherent fat, and the adventitia were dissected free from the arteries. Each artery was then cut lengthwise, pinned flat to expose the intimal (luminal) surface, stained with Sudan IV, and then photographed. Sudan IV is a fat soluble red dye that stains atherosclerotic plaques on the intimal surface of arteries. The stained aortas of rabbits #2 and #5 revealed a prevalence of atherosclerotic lesions along the length of the aortas and particularly in the portion of the aortas from the thoracic region. The aortas of rabbits #2 and #5 were similar to those of unvaccinated rabbits on a cholesterol-supplemented, atherogenic diet (such as rabbits #10, #12, and #13). In contrast, the aortas of rabbits #3 and #6 had a much smoother and more uniform appearance on the intimal surface owing to a lower incidence of lesions, including the portion of the aorta from the thoracic region.

To quantify the noticeable difference in the presence of atherosclerotic lesions in the aortas of rabbits #2 and #5 and lack thereof in the aortas of rabbits #3 and #6, the surface area of the pinned aortas and that of the aortic lesions was determined from photographs by planar morphometry (Daley et al., 1994) using a digitizing tablet with associated software (THE MORPHOMETER™, Woods Hole Educational Associates, Woods Hole, Mass.). The percentage of the surface area of the aortas covered by lesions was determined to be 44.8% for rabbit #2, 50.9% for rabbit #5, 14.2% for rabbit #3, and 14.4% for rabbit #6.

In summary, rabbits #2 and #5, did not produce detectable anti-rabbit CETP antibody as determined by ELISA using the rabbit CETP 477–496 peptide after 220 days on the vaccination protocol described above and shown in FIG. 6, and these rabbits developed significant atherosclerotic lesions over the intimal surface of their aortas (44.8% and 50.9%, respectively) after eating a diet supplemented with cholesterol for about 17 weeks. In contrast, rabbits #3 and #6, which probably produced anti-rabbit CETP antibody, had noticeably less surface area of their aortas covered with atherosclerotic lesion (14.2% and 14.4%, respectively) after approximately 17 weeks on an elevated cholesterol diet.

EXAMPLE IV

The results of the above experiment using a rabbit model for atherosclerosis indicate that the plasmid-based vaccines of this invention may be used to prevent or treat atherosclerosis in other vertebrates. By analogy to the treatment for inhibiting atherosclerosis in rabbits illustrated in Example III, similar plasmid constructs may be made for other vertebrates, including humans. Such plasmids encode an immunogenic fusion polypeptide comprising a universal or broad range T cell epitope, such as from tetanus toxoid or diphtheria toxoid, linked in the same reading frame to at least one, more preferably two, B cell epitopes of the endogenous CETP of the individual. An example of a plasmid-based vaccine for endogenous human CETP contains a DNA sequence encoding a translation initiating methionine linked to a TT polypeptide, such as in nucleotides 10–54 of SEQ ID NO:5, which is linked in the same reading frame (with or without intervening linker sequences) to a DNA sequence encoding regions of human CETP analogous to those used in the rabbit CETP plasmid-based vaccine, such as nucleotides 1045–1101 and 1381–1428 of SEQ ID NO:3 encoding amino acids 349–367 and 461–476 of SEQ ID NO:4, respectively. Preferably, the DNA sequence in the plasmid for use as a vaccine against human endogenous CETP also includes regions as shown in FIG. 5, such as translational start and stop codons and flanking restriction endonuclease sites that are commonly employed for plasmid construction and gene expression.

EXAMPLE V

In another aspect of this invention, plasmid-based vaccines can be made in which a plasmid encodes a universal or broad range T cell epitope portion linked in frame to a B cell epitope portion comprising one or more B cell epitopes of a non-endogenous CETP. Such non-endogenous, vaccinating B cell epitopes encoded by plasmids of this invention may be derived from another species, another allele, or of non-natural origin (i.e., a synthetic sequence); in such cases the amino acid sequence of the non-endogenous, vaccinating B cell epitope(s) is slightly different from that of the endogenous CETP of the individual to be vaccinated. For example, a vaccinating, non-endogenous B cell epitope that is slightly different from that of a B cell epitope of the endogenous CETP protein is one which has an amino acid sequence which differs from the corresponding B cell epitope of the endogenous CETP at a few, for example, 1, 2, 3, 4, 5, or 6, residues.

Another example of a non-endogenous, vaccinating B cell epitope that is slightly different from a B cell epitope of an endogenous CETP is one that contains one or more conservative changes in amino acid sequence at one or more residues known to be important for a CETP activity and/or for antibody binding (see, for example, Hesler et al., *J. Biol. Chem.*, 263: 5020–5023 (1988); Wang et al., *J. Biol. Chem.*, 267: 17487–17490 (1992); Wang et al., *J. Biol. Chem.*, 268: 1955–1959 (1993)) or at one or more residues known to differ at analogous positions in the amino acid sequence of CETP encoded by other alleles or genes of other species (see, for example, Nagashima et al., *J. Lipid Res.*, 29: 1643–1649 (1988); Kotake et al., *J. Lipid Res.*, 37: 599–605 (1996); Drayna et al., *Nature*, 327: 632–634 (1987)).

An example of a plasmid-based vaccine for humans containing non-endogenous, vaccinating B cell epitopes is the above-described plasmid pCMV-CETP/TT which uses DNA sequences encoding B cell epitopes from rabbit CETP. Another example for use in humans, is a similar plasmid where the encoded B cell epitopes are not derived from a particular species, but are synthetic versions that are slightly different from those encoded by the corresponding human CETP DNA sequences.

While not desiring to be bound by any particular theory, the use of one or more non-endogenous, vaccinating B cell epitopes containing an amino acid sequence which is slightly different from that of a B cell epitope of the endogenous protein (i.e., endogenous CETP) may elicit autoantibodies more effectively than if the endogenous B cell epitopes are employed. Such non-endogenous, vaccinating B cell epitopes (1) elicit production of antibodies in the vaccinated individual and (2) these elicited antibodies, or a subset thereof, bind endogenous CETP. For example, to test whether a plasmid-based vaccine of this invention elicits autoantibodies to CETP in a human, human CETP transgenic mice (for example, commercially available BIODIGM™-CETP mice, Pharmakon USA, Waverly, Pa.) are vaccinated with a plasmid construct according to this invention and the production of antibodies recognizing human CETP is quantitated. Quantitation of anti-human CETP antibodies is readily determined by a variety of methods, including Western blotting sera from a vaccinated animal to electrophoresed human CETP; or ELISA where sera from the vaccinated animal is assayed for the ability to bind human CETP or peptide fragment(s) thereof, or isolating CETP from the blood of vaccinated animals and assaying for antibody bound to the CETP.

Bacterial cell cultures (*E. coli*) bearing plasmids pCMV-LUC and pCMV-CETP/TT prepared as described above were deposited Apr. 26, 1996 under the terms of the Budapest Treaty with the American Type Culture Collection, 12301 Parklawn Drive, Rockville, Md. They were assigned accession numbers 98037 and 98038, respectively.

All documents and publications cited above are incorporated herein by reference.

What is claimed is:

1. A DNA immunogenic composition comprising a nucleotide sequence coding for an immunogenic polypeptide, which nucleotide sequence includes at least one segment coding for a B cell epitope of cholesteryl ester transfer protein (CETP) linked in-frame with at least one segment coding for a broad range helper T cell epitope, which nucleotide sequence is operably linked to a promoter sequence suitable for directing the transcription of the nucleotide sequence in a mammalian cell.

2. The DNA immunogenic composition according to claim 1 wherein said at least one segment coding for a B cell epitope of CETP encodes a B cell epitope of human CETP and consists of 5–8 consecutive amino acids of SEQ ID NO:4.

3. The DNA immunogenic composition according to claim 1 wherein said B cell epitope comprises a carboxyl terminal region of CETP, involved in neutral lipid binding or neutral lipid transfer activity.

4. The DNA immunogenic composition according to claim 1 wherein the helper T cell epitope comprises a helper T cell epitope obtained from an antigenic peptide selected from the group consisting of tetanus toxoid, diphtheria toxin, pertussis vaccine, Bacile Calmette-Guerin (BCG), polio vaccine, measles vaccine, mumps vaccine, rubella vaccine, purified protein derivative of tuberculin, keyhole limpet hemocyanin, and combinations thereof.

5. The DNA immunogenic composition according to claim 1 wherein the immunogenic polypeptide includes two B cell epitopes of CETP.

6. The DNA immunogenic composition according to claim 5 which includes a DNA segment coding for amino acids 463 through 475 of SEQ ID NO: 4 and a DNA segment coding for amino acids 349 through 367 of SEQ ID NO: 4.

7. The DNA immunogenic composition according to claim 5 which includes a DNA segment coding for amino acids 461 through 476 of SEQ ID NO: 4 and a DNA segment coding for amino acids 349 through 367 of SEQ ID NO: 4.

8. The DNA immunogenic composition according to claim 1, wherein said at least one segment coding for a broad helper T cell epitope encodes amino acids 2 through 15 of SEQ ID NO: 7.

9. The DNA immunogenic composition according to claim 1, wherein said nucleotide sequence coding for an immunogenic polypeptide encodes the amino acid sequence of SEQ ID NO:7.

10. The DNA immunogenic composition according to claim 1, wherein the promoter is a cytomegalovirus immediate early promoter/enhancer.

11. A DNA immunogenic composition comprising a nucleotide sequence comprising:
    (a) an immediate early promoter/enhancer region of cytomegalovirus (CMV), operably linked to
    (b) a structural DNA segment encoding an immunogenic polypeptide and comprising:
        (i) a DNA segment encoding amino acids 2 through 15 of SEQ ID NO: 7,
        (ii) a DNA segment encoding amino acids 463 through 475 of SEQ ID NO: 4, and
        (iii) a DNA segment encoding amino acids 349 through 367 of SEQ ID NO: 4,
    which DNA segments (i), (ii) and (iii) are linked in-frame.

12. A DNA immunogenic composition comprising a nucleotide sequence comprising:
    (a) an immediate early promoter/enhancer region of cytomegalovirus (CMV), operably linked to
    (b) a structural DNA segment encoding an immunogenic polypeptide and comprising:
        (i) a DNA segment encoding amino acids 2 through 15 of SEQ ID NO: 7,
        (ii) a DNA segment encoding amino acids 461 through 476 of SEQ ID NO: 4, and
        (iii) a DNA segment encoding amino acids 349 through 367 of SEQ ID NO: 4,
    which DNA segments (i), (ii) and (iii) are linked in-frame.

13. A DNA immunogenic composition comprising a nucleotide sequence coding for an immunogenic polypeptide, which nucleotide sequence comprises a first segment coding for a broad range helper T cell epitope linked in frame with a second segment coding for a first B cell epitope of cholesteryl ester transfer protein (CETP) having the nucleotide sequence of nucleotides 55 through 111 of SEQ ID NO:5 and a third segment coding for a second B cell epitope of CETP having the nucleotide sequence of nucleotides 112 through 159 of SEQ ID NO:5, wherein the nucleotide sequence coding for the immunogenic polypeptide is operably linked to a promoter sequence suitable for directing the transcription of the nucleotide sequence in a mammalian cell.

14. The DNA immunogenic composition according to claim 13 wherein the nucleotide sequence comprises the nucleotide sequence of SEQ ID NO:5.

15. A DNA immunogenic composition comprising a nucleotide sequence coding for an immunogenic polypeptide, which nucleotide sequence comprises a first segment encoding a broad range helper T cell epitope linked in-frame with a second segment coding for a first B cell epitope of cholesteryl ester transfer protein (CETP) having the nucleotide sequence of nucleotides 1045 through 1101 of SEQ ID NO:3 and a third segment coding for a second B cell epitope of CETP having the nucleotide sequence of nucleotides 1387 through 1425 of SEQ ID NO:3, wherein the nucleotide sequence coding for the immunogenic polypeptide is operably linked to a promoter sequence suitable for directing the transcription of the nucleotide sequence in a mammalian cell.

16. A DNA immunogenic composition comprising a nucleotide sequence coding for an immunogenic polypeptide, which nucleotide sequence comprises a first segment coding for a broad range helper T cell epitope linked in-frame with a second segment coding for a first B cell epitope of cholesteryl ester transfer protein (CETP) having the nucleotide sequence of nucleotides 1045 through 1101 of SEQ ID NO:3 and a third segment coding for a second B cell epitope of CETP having the nucleotide sequence of nucleotides 1381 through 1428 of SEQ ID NO:3, wherein the nucleotide sequence coding for the immunogenic polypeptide is operably linked to a promoter sequence suitable for directing the transcription of the nucleotide sequence in a mammalian cell.

17. A DNA immunogenic composition comprising a nucleotide sequence coding for an immunogenic polypeptide, said nucleotide sequence being operably linked to a promoter sequence suitable for directing the transcription of said nucleotide sequence in a mammalian cell, said immunogenic polypeptide comprising a B cell epitope portion, wherein said B cell epitope portion comprises at least one B cell epitope of cholesteryl ester transfer protein (CETP), and a broad range helper T cell epitope portion, wherein said broad range helper T cell epitope portion comprises at least one broad range helper T cell epitope.

18. The DNA immunogenic composition according to claim 17, wherein said at least one B cell epitope of CETP consists of 5–26 consecutive amino acids of SEQ ID NO:4.

19. The DNA immunogenic composition according to claim 17, wherein said at least one broad range helper T cell epitope is a broad range helper T cell epitope obtained from an immunogenic peptide selected from the group consisting of tetanus toxoid, diphtheria toxin, pertussis vaccine, Bacile Calmette-Guerin (BCG), polio vaccine, measles vaccine, mumps vaccine, rubella vaccine, purified protein derivative of tuberculin, and combinations thereof.

20. The DNA immunogenic composition according to claim 17, wherein said immunogenic polypeptide includes two B cell epitopes of CETP.

* * * * *

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 1488 base pairs
      (B) TYPE:nucleic acid
      (C) STRANDEDNESS:single
      (D) TOPOLOGY: linear (ii) MOLECULE TYPE:cDNA (iii) HYPOTHETICAL:

(iv) ANTI-SENSE:

(ix) FEATURE: Structural coding sequence for
     mature rabbit CETP
    (A) NAME/KEY:
    (B) LOCATION:

(x) PUBLICATION INFORMATION:
    (A) AUTHORS:Nagashima, Mariko, et al.
    (B) TITLE:Cloning and mRNA tissue distribution of rabbit
        cholesteryl ester transfer protein
    (C) JOURNAL:J. Lipid Res.
    (D) VOLUME:29
    (E) ISSUE:
    (F) PAGES:1643 - 1649
    (G) DATE:1988
    (K) RELEVANT RESIDUES IN SEQ ID NO:1: FROM 1 TO 1488

(xi) SEQUENCE DESCRIPTION: SEQ ID NO: 1:

| | | |
|---|---|---|
| TGTCCCAAAG GCGCCTCCTA CGAGGCTGGC ATCGTGTGTC GCATCACCAA | | 50 |
| GCCCGCCCTC TTGGTGTTGA ACCAAGAGAC GGCCAAGGTG GTCCAGACGG | | 100 |
| CCTTCCAGCG CGCCGGCTAT CCGGACGTCA GCGGCGAGAG GGCCGTGATG | | 150 |
| CTCCTCGGCC GGGTCAAGTA CGGGCTGCAC AACCTCCAGA TCAGCCACCT | | 200 |
| GTCCATCGCC AGCAGCCAGG TGGAGCTGGT GGACGCCAAG ACCATCGACG | | 250 |
| TCGCCATCCA GAACGTGTCC GTGGTCTTCA AGGGGACCCT GAACTACAGC | | 300 |
| TACACGAGTG CCTGGGGGTT GGGCATCAAT CAGTCTGTCG ACTTCGAGAT | | 350 |
| CGACTCTGCC ATTGACCTCC AGATCAACAC AGAGCTGACC TGCGACGCTG | | 400 |
| GCAGTGTGCG CACCAATGCC CCCGACTGCT ACCTGGCTTT CCATAAACTG | | 450 |
| CTCCTGCACC TCCAGGGGGA GCGCGAGCCG GGTGGCTCA AGCAGCTCTT | | 500 |
| CACAAACTTC ATCTCCTTCA CCCTGAAGCT GATTCTGAAG CGACAGGTCT | | 550 |
| GCAATGAGAT CAACACCATC TCCAACATCA TGGCTGACTT TGTCCAGACG | | 600 |
| AGGGCCGCCA GCATCCTCTC AGATGGAGAC ATCGGGGTGG ACATTTCCGT | | 650 |
| GACGGGGGCC CCTGTCATCA CAGCCACCTA CCTGGAGTCC ATCACAAGG | | 700 |
| GTCACTTCAC GCACAAGAAC GTCTCCGAGG CCTTCCCCCT CCGCGCCTTC | | 750 |
| CCGCCCGGTC TTCTGGGGGA CTCCCGCATG CTCTACTTCT GGTTCTCCGA | | 800 |
| TCAAGTGCTC AACTCCCTGG CCAGGGCCGC CTTCCAGGAG GGCCGTCTCG | | 850 |
| TGCTCAGCCT GACAGGGGAT GAGTTCAAGA AGTGCTGGA GACCCAGGGT | | 900 |
| TTCGACACCA ACCAGGAAAT CTTCCAGGAG CTTTCCAGAG GCCTTCCCAC | | 950 |
| CGGCCAGGCC CAGGTAGCCG TCCACTGCCT TAAGGTGCCC AAGATCTCCT | | 1000 |
| GCCAGAACCG GGGTGTCGTG GTGTCTTCTT CCGTCGCCGT GACGTTCCGC | | 1050 |
| TTCCCCCGCC CAGATGGCCG AGAAGCTGTG GCCTACAGGT TGAGGAGGA | | 1100 |
| TATCATCACC ACCGTCCAGG CCTCCTACTC CCAGAAAAAG CTCTTCCTAC | | 1150 |
| ACCTCTTGGA TTTCCAGTGC GTGCCGGCCA GCGGAAGGGC AGGCAGCTCA | | 1200 |
| GCAAATCTCT CCGTGGCCCT CAGGACTGAG GCTAAGGCTG TTTCCAACCT | | 1250 |
| GACTGAGAGC CGCTCCGAGT CCCTGCAGAG CTCTCTCCGC TCCCTGATCG | | 1300 |
| CCACGGTGGG CATCCCGGAG GTCATGTCTC GGCTCGAGGT GGCGTTCACA | | 1350 |
| GCCCTCATGA ACAGCAAAGG CCTGGACCTC TTCGAAATCA TCAACCCCGA | | 1400 |

```
GATTATCACT CTCGATGGCT GCCTGCTGCT GCAGATGGAC TTCGGTTTTC          1450

CCAAGCACCT GCTGGTGGAT TTCCTGCAGA GCCTGAGC                      1488
```

(2) INFORMATION FOR SEQ ID NO:2:

(i) SEQUENCE CHARACTERISTICS:
        (A) LENGTH:496 amino acids
        (B) TYPE:amino acid
        (D) TOPOLOGY:linear (ii) MOLECULE TYPE:protein (iii) HYPOTHETICAL:

(iv) ANTI-SENSE:

(ix) FEATURE:
        (A) NAME/KEY:Amino acid sequence for mature
            rabbit CETP protein.
        (B) LOCATION:

(x) PUBLICATION INFORMATION:
        (A) AUTHORS:Nagashima, Mariko, et al.
        (B) TITLE:Cloning and mRNA tissue
            distribution of rabbit
            cholesteryl ester transfer
            protein
        (C) JOURNAL:J. Lipid Res.
        (D) VOLUME:29
        (E) ISSUE:
        (F) PAGES:1643 - 1649
        (G) DATE:1988
        (K) RELEVANT RESIDUES IN SEQ ID NO:2: FROM 1 TO 496

(xi) SEQUENCE DESCRIPTION: SEQ ID NO:2:

```
Cys Pro Lys Gly Ala Ser Tyr Glu Ala Gly Ile Val Cys
1               5                   10

Arg Ile Thr Lys Pro Ala Leu Leu Val Leu Asn Gln Glu
    15              20                  25

Thr Ala Lys Val Val Gln Thr Ala Phe Gln Arg Ala Gly
                30              35

Tyr Pro Asp Val Ser Gly Glu Arg Ala Val Met Leu Leu
40                  45                  50

Gly Arg Val Lys Tyr Gly Leu His Asn Leu Gln Ile Ser
        55              60                  65

His Leu Ser Ile Ala Ser Ser Gln Val Glu Leu Val Asp
                70              75

Ala Lys Thr Ile Asp Val Ala Ile Gln Asn Val Ser Val
    80              85                  90

Val Phe Lys Gly Thr Leu Asn Tyr Ser Tyr Thr Ser Ala
            95              100

Trp Gly Leu Gly Ile Asn Gln Ser Val Asp Phe Glu Ile
105                 110                 115

Asp Ser Ala Ile Asp Leu Gln Ile Asn Thr Glu Leu Thr
            120             125                 130

Cys Asp Ala Gly Ser Val Arg Thr Asn Ala Pro Asp Cys
                135                 140

Tyr Leu Ala Phe His Lys Leu Leu Leu His Leu Gln Gly
        145             150                 155

Glu Arg Glu Pro Gly Trp Leu Lys Gln Leu Phe Thr Asn
                160             165

Phe Ile Ser Phe Thr Leu Lys Leu Ile Leu Lys Arg Gln
```

```
         170                 175                 180
    Val Cys Asn Glu Ile Asn Thr Ile Ser Asn Ile Met Ala
                 185                 190                 195
    Asp Phe Val Gln Thr Arg Ala Ala Ser Ile Leu Ser Asp
                     200                 205
    Gly Asp Ile Gly Val Asp Ile Ser Val Thr Gly Ala Pro
         210                 215                 220
    Val Ile Thr Ala Thr Tyr Leu Glu Ser His His Lys Gly
                 225                 230
    His Phe Thr His Lys Asn Val Ser Glu Ala Phe Pro Leu
    235                 240                 245
    Arg Ala Phe Pro Pro Gly Leu Leu Gly Asp Ser Arg Met
                 250                 255                 260
    Leu Tyr Phe Trp Phe Ser Asp Gln Val Leu Asn Ser Leu
                     265                 270
    Ala Arg Ala Ala Phe Gln Glu Gly Arg Leu Val Leu Ser
         275                 280                 285
    Leu Thr Gly Asp Glu Phe Lys Lys Val Leu Glu Thr Gln
                 290                 295
    Gly Phe Asp Thr Asn Gln Glu Ile Phe Gln Glu Leu Ser
    300                 305                 310
    Arg Gly Leu Pro Thr Gly Gln Ala Gln Val Ala Val His
         315                 320                 325
    Cys Leu Lys Val Pro Lys Ile Ser Cys Gln Asn Arg Gly
                     330                 335
    Val Val Val Ser Ser Val Ala Val Thr Phe Arg Phe
         340                 345                 350
    Pro Arg Pro Asp Gly Arg Glu Ala Val Ala Tyr Arg Phe
                 355                 360
    Glu Glu Asp Ile Ile Thr Thr Val Gln Ala Ser Tyr Ser
    365                 370                 375
    Gln Lys Lys Leu Phe Leu His Leu Leu Asp Phe Gln Cys
                 380                 385                 390
    Val Pro Ala Ser Gly Arg Ala Gly Ser Ser Ala Asn Leu
                     395                 400
    Ser Val Ala Leu Arg Thr Glu Ala Lys Ala Val Ser Asn
         405                 410                 415
    Leu Thr Glu Ser Arg Ser Glu Ser Leu Gln Ser Ser Leu
                 420                 425
    Arg Ser Leu Ile Ala Thr Val Gly Ile Pro Glu Val Met
    430                 435                 440
    Ser Arg Leu Glu Val Ala Phe Thr Ala Leu Met Asn Ser
                 445                 450                 455
    Lys Gly Leu Asp Leu Phe Glu Ile Ile Asn Pro Glu Ile
                     460                 465
    Ile Thr Leu Asp Gly Cys Leu Leu Gln Met Asp Phe
         470                 475                 480
    Gly Phe Pro Lys His Leu Leu Val Asp Phe Leu Gln Ser
                 485                 490
    Leu Ser
    495

(2) INFORMATION FOR SEQ ID NO: 3:
```

```
    (i) SEQUENCE CHARACTERISTICS:
        (A) LENGTH:   1428 base pairs
        (B) TYPE:nucleic acid
        (C) STRANDEDNESS: single
        (D) TOPOLOGY: linear (ii) MOLECULE TYPE:cDNA (iii) HYPOTHETICAL:

(iv) ANTI-SENSE:

(ix) FEATURE:
        (A) NAME/KEY:Structural coding sequence for
            mature human CETP
        (B) LOCATION:

(x) PUBLICATION INFORMATION:
        (A) AUTHORS:Drayna, Dennis, et al.
        (B) TITLE: Cloning and sequencing of
            human cholesteryl ester
            transfer cDNA
        (C) JOURNAL:Nature
        (D) VOLUME:327
        (E) ISSUE:
        (F) PAGES:632 - 634
        (G) DATE:18-JUN-1987
        (K) RELEVANT RESIDUES IN SEQ ID NO:3:FROM 1 TO 1428

(xi) SEQUENCE DESCRIPTION: SEQ ID NO:3:
```

| | | |
|---|---|---|
| TGCTCCAAAG GCACCTCGCA CGAGGCAGGC ATCGTGTGCC GCATCACCAA | 50 |
| GCCTGCCCTC CTGGTGTTGA ACCACGAGAC TGCCAAGGTG ATCCAGACCG | 100 |
| CCTTCCAGCG AGCCAGCTAC CCAGATATCA CGGGCGAGAA GGCCATGATG | 150 |
| CTCCTTGGCC AAGTCAAGTA TGGGTTGCAC AACATCCAGA TCAGCCACTT | 200 |
| GTCCATCGCC AGCAGCCAGG TGGAGCTGGT GGAAGCCAAG TCCATTGATG | 250 |
| TCTCCATTCA GAACGTGTCT GTGGTCTTCA AGGGGACCCT GAAGTATGGC | 300 |
| TACACCACTG CCTGGTGGCT GGGTATTGAT CAGTCCATTG ACTTCGAGAT | 350 |
| CGACTCTGCC ATTGACCTCC AGATCAACAC ACAGCTGACC TGTGACTCTG | 400 |
| GTAGAGTGCG GACCGATGCC CCTGACTGCT ACCTGTCTTT CCATAAGCTG | 450 |
| CTCCTGCATC TCCAAGGGGA GCGAGAGCCT GGGTGGATCA AGCAGCTGTT | 500 |
| CACAAATTTC ATCTCCTTCA CCCTGAAGCT GGTCCTGAAG GGACAGATCT | 550 |
| GCAAAGAGAT CAACGTCATC TCTAACATCA TGGCCGATTT TGTCCAGACA | 600 |
| AGGGCTGCCA GCATCCTTTC AGATGGAGAC ATTGGGGTGG ACATTTCCCT | 650 |
| GACAGGTGAT CCCGTCATCA CAGCCTCCTA CCTGGAGTCC CATCACAAGG | 700 |
| GTCATTTCAT CTACAAGAAT GTCTCAGAGG ACCTCCCCCT CCCCACCTTC | 750 |
| TCGCCCACAC TGCTGGGGGA CTCCCGCATG CTGTACTTCT GGTTCTCTGA | 800 |
| GCGAGTCTTC CACTCGCTGG CCAAGGTAGC TTTCCAGGAT GGCCGCCTCA | 850 |
| TGCTCAGCCT GATGGGAGAC GAGTTCAAGG CAGTGCTGGA GACCTGGGGC | 900 |
| TTCAACACCA ACCAGGAAAT CTTCCAAGAG GTTGTCGGCG GCTTCCCCAG | 950 |
| CCAGGCCCAA GTCACCGTCC ACTGCCTCAA GATGCCCAAG ATCTCCTGCC | 1000 |
| AAAACAAGGG AGTCGTGGTC AATTCTTCAG TGATGGTGAA ATTCCTCTTT | 1050 |
| CCACGCCCAG ACCAGCAACA TTCTGTAGCT TACACATTTG AAGAGGATAT | 1100 |
| CGTGACTACC GTCCAGGCCT CCTATTCTAA GAAAAAGCTC TTCTTAAGCC | 1150 |
| TCTTGGATTT CCAGATTACA CCAAAGACTG TTTCCAACTT GACTGAGAGC | 1200 |

```
AGCTCCGAGT CCATCCAGAG CTTCCTGCAG TCAATGATCA CCGCTGTGGG            1250

CATCCCTGAG GTCATGTCTC GGCTCGAGGT AGTGTTTACA GCCCTCATGA            1300

ACAGCAAAGG CGTGAGCCTC TTCGACATCA TCAACCCTGA GATTATCACT            1350

CGAGATGGCT TCCTGCTGCT GCAGATGGAC TTTGGCTTCC CTGAGCACCT            1400

GCTGGTGGAT TTCCTCCAGA GCTTGAGC                                   1428
```

(2) INFORMATION FOR SEQ ID NO: 4:

(i) SEQUENCE CHARACTERISTICS:
        (A) LENGTH: 476 amino acids
        (B) TYPE:amino acid
        (D) TOPOLOGY: linear (ii) MOLECULE TYPE:peptide (iii) HYPOTHETICAL:

(iv) ANTI-SENSE:

(ix) FEATURE:
        (A) NAME/KEY:Amino acid sequence of mature human
            CETP
        (B) LOCATION:

(x) PUBLICATION INFORMATION:
        (A) AUTHORS:Drayna, Dennis, et al.
        (B) TITLE:Cloning and sequencing of human
            cholesteryl ester transfer cDNA
        (C) JOURNAL:Nature
        (D) VOLUME:327
        (E) ISSUE:
        (F) PAGES:632 - 634
        (G) DATE:18-JUN-1987
        (K) RELEVANT RESIDUES IN SEQ ID NO:4: FROM 1 TO 476

(xi) SEQUENCE DESCRIPTION: SEQ ID NO: 4:

```
Cys Ser Lys Gly Thr Ser His Glu Ala Gly Ile Val Cys
 1               5                  10

Arg Ile Thr Lys Pro Ala Leu Leu Val Leu Asn His Glu
        15                  20                  25

Thr Ala Lys Val Ile Gln Thr Ala Phe Gln Arg Ala Ser
                30                  35

Tyr Pro Asp Ile Thr Gly Glu Lys Ala Met Met Leu Leu
 40                  45                  50

Gly Gln Val Lys Tyr Gly Leu His Asn Ile Gln Ile Ser
            55                  60                  65

His Leu Ser Ile Ala Ser Ser Gln Val Glu Leu Val Glu
                70                  75

Ala Lys Ser Ile Asp Val Ser Ile Gln Asn Val Ser Val
        80                  85                  90

Val Phe Lys Gly Thr Leu Lys Tyr Gly Tyr Thr Thr Ala
                95                  100

Trp Trp Leu Gly Ile Asp Gln Ser Ile Asp Phe Glu Ile
105                 110                 115

Asp Ser Ala Ile Asp Leu Gln Ile Asn Thr Gln Leu Thr
        120                 125                 130

Cys Asp Ser Gly Arg Val Arg Thr Asp Ala Pro Asp Cys
                135                 140

Tyr Leu Ser Phe His Lys Leu Leu His Leu Gln Gly
        145                 150                 155
```

-continued

```
Glu Arg Glu Pro Gly Trp Ile Lys Gln Leu Phe Thr Asn
            160                 165

Phe Ile Ser Phe Thr Leu Lys Leu Val Leu Lys Gly Gln
170                 175                 180

Ile Cys Lys Glu Ile Asn Val Ile Ser Asn Ile Met Ala
                185                 190                 195

Asp Phe Val Gln Thr Arg Ala Ala Ser Ile Leu Ser Asp
                    200                 205

Gly Asp Ile Gly Val Asp Ile Ser Leu Thr Gly Asp Pro
    210                 215                 220

Val Ile Thr Ala Ser Tyr Leu Glu Ser His His Lys Gly
                225                 230

His Phe Ile Tyr Lys Asn Val Ser Glu Asp Leu Pro Leu
235                 240                 245

Pro Thr Phe Ser Pro Thr Leu Leu Gly Asp Ser Arg Met
            250                 255                 260

Leu Tyr Phe Trp Phe Ser Glu Arg Val Phe His Ser Leu
                265                 270

Ala Lys Val Ala Phe Gln Asp Gly Arg Leu Met Leu Ser
275                 280                 285

Leu Met Gly Asp Glu Phe Lys Ala Val Leu Glu Thr Trp
            290                 295

Gly Phe Asn Thr Asn Gln Glu Ile Phe Gln Glu Val Val
300                 305                 310

Gly Gly Phe Pro Ser Gln Ala Gln Val Thr Val His Cys
            315                 320                 325

Leu Lys Met Pro Lys Ile Ser Cys Gln Asn Lys Gly Val
                330                 335

Val Val Asn Ser Ser Val Met Val Lys Phe Leu Phe Pro
340                 345                 350

Arg Pro Asp Gln Gln His Ser Val Ala Tyr Thr Phe Glu
            355                 360

Glu Asp Ile Val Thr Thr Val Gln Ala Ser Tyr Ser Lys
365                 370                 375

Lys Lys Leu Phe Leu Ser Leu Leu Asp Phe Gln Ile Thr
            380                 385                 390

Pro Lys Thr Val Ser Asn Leu Thr Glu Ser Ser Ser Glu
                395                 400

Ser Ile Gln Ser Phe Leu Gln Ser Met Ile Thr Ala Val
    405                 410                 415

Gly Ile Pro Glu Val Met Ser Arg Leu Glu Val Val Phe
            420                 425

Thr Ala Leu Met Asn Ser Lys Gly Val Ser Leu Phe Asp
430                 435                 440

Ile Ile Asn Pro Glu Ile Ile Thr Arg Asp Gly Phe Leu
            445                 450                 455

Leu Leu Gln Met Asp Phe Gly Phe Pro Glu His Leu Leu
                460                 465

Val Asp Phe Leu Gln Ser Leu Ser
    470                 475
```

(2) INFORMATION FOR SEQ ID NO: 5:

(i) SEQUENCE CHARACTERISTICS:

(A) LENGTH: 169 base pairs
        (B) TYPE:nucleic acid
        (C) STRANDEDNESS:single
        (D) TOPOLOGY: linear (ii) MOLECULE TYPE:

(iii) HYPOTHETICAL:

(iv) ANTI-SENSE:

(ix) FEATURE:
        (A) NAME/KEY:
        (B) LOCATION:

(xi) SEQUENCE DESCRIPTION: SEQ ID NO:5:

GCGGCCGCCA TGCAGTACAT CAAGGCCAAC TCCAAGTTCA TCGGCATCAC          50

GGAGCGCTTC CCCCGCCCAG ATGGCCGAGA AGCTGTGGCC TACAGGTTTG         100

AGGAGGATAT CTTCGGTTTT CCCAAGCACC TGCTGGTGGA TTTCCTGCAG         150

AGCCTGAGCT AGCGGCCGC                                           169

(2) INFORMATION FOR SEQ ID NO: 6:

(i) SEQUENCE CHARACTERISTICS:
        (A) LENGTH:169 base pairs
        (B) TYPE:nucleic acid
        (C) STRANDEDNESS:single
        (D) TOPOLOGY: linear (ii) MOLECULE TYPE:DNA (iii) HYPOTHETICAL:

(iv) ANTI-SENSE:

(ix) FEATURE:
        (A) NAME/KEY:Complementary strand to SEQ ID NO:5
        (B) LOCATION: 1 to 169

(xi) SEQUENCE DESCRIPTION: SEQ ID NO:6:

GCGGCCGCTA GCTCAGGCTC TGCAGGAAAT CCACCAGCAG GTGCTTGGGA          50

AAACCGAAGA TATCCTCCTC AAACCTGTAG GCCACAGCTT CTCGGCCATC         100

TGGGCGGGGG AAGCGCTCCG TGATGCCGAT GAACTTGGAG TTGGCCTTGA         150

TGTACTGCAT CGCGGCCGC                                           169

(2) INFORMATION FOR SEQ ID NO:7:

(i) SEQUENCE CHARACTERISTICS:
        (A) LENGTH:50 amino acids
        (B) TYPE: amino acid
        (D) TOPOLOGY:  linear (ii) MOLECULE TYPE:  peptide (iii) HYPOTHETICAL:

(iv) ANTI-SENSE:

(ix) FEATURE:  amino acid sequence of peptide encoded
           by bases 10 to 159 of SEQ ID NO:5
        (A) NAME/KEY:
        (B) LOCATION:

(xi) SEQUENCE DESCRIPTION: SEQ ID NO:7:

Met Gln Tyr Ile Lys Ala Asn Ser Lys Phe Ile Gly Ile
1               5                  10

Thr Glu Arg Phe Pro Arg Pro Asp Gly Arg Glu Ala Val

```
        15                  20                  25
Ala Tyr Arg Phe Glu Glu Asp Ile Phe Gly Phe Pro Lys
                30                  35

His Leu Leu Val Asp Phe Leu Gln Ser Leu Ser
40                  45                  50

(2) INFORMATION FOR SEQ ID NO:8:

(i) SEQUENCE CHARACTERISTICS:
         (A) LENGTH:  1608 base pairs
         (B) TYPE:  nucleic acid
         (C) STRANDEDNESS:  Single
         (D) TOPOLOGY:  linear (ii) MOLECULE TYPE:

(iii) HYPOTHETICAL:

(iv) ANTI-SENSE:

(ix) FEATURE:
         (A) NAME/KEY:  translational stop codon
         (B) LOCATION:  1606 - 1608

(xi) SEQUENCE DESCRIPTION: SEQ ID NO:8:
```

| | |
|---|---|
| GGCGCTGATG ATGTTGTTGA TTCTTCTAAA TCTTTTGTGA TGGAAAACTT | 50 |
| TTCTTCGTAC CACGGGACTA AACCTGGTTA TGTAGATTCC ATTCAAAAAG | 100 |
| GTATACAAAA GCCAAAATCT GGTACACAAG GAAATTATGA CGATGATTGG | 150 |
| AAAGGGTTTT ATAGTACCGA CAATAAATAC GACGCTGCGG GATACTCTGT | 200 |
| AGATAATGAA ACCCGCTCT CTGGAAAAGC TGGAGGCGTG GTCAAAGTGA | 250 |
| CGTATCCAGG ACTGACGAAG GTTCTCGCAC TAAAAGTGGA TAATGCCGAA | 300 |
| ACTATTAAGA AAGAGTTAGG TTTAAGTCTC ACTGAACCGT TGATGGAGCA | 350 |
| AGTCGGAACG GAAGAGTTTA TCAAAAGGTT CGGTGATGGT GCTTCGCGTG | 400 |
| TAGTGCTCAG CCTTCCCTTC GCTGAGGGGA GTTCTAGCGT TGAATATATT | 450 |
| AATAACTGGG AACAGGCGAA AGCGTTAAGC GTAGAACTTG AGATTAATTT | 500 |
| TGAAACCCGT GGAAAACGTG GCCAAGATGC GATGTATGAG TATATGGCTC | 550 |
| AAGCCTGTGC AGGAAATCGT GTCAGGCGAT CAGTAGGTAG CTCATTGTCA | 600 |
| TGCATAAATC TTGATTGGGA TGTCATAAGG GATAAAACTA AGACAAAGAT | 650 |
| AGAGTCTTTG AAAGAGCATG GCCCTATCAA AAATAAAATG AGCGAAAGTC | 700 |
| CCAATAAAAC AGTATCTGAG GAAAAAGCTA ACAATACCT AGAAGAATTT | 750 |
| CATCAAACGG CATTAGAGCA TCCTGAATTG TCAGAACTTA AAACCGTTAC | 800 |
| TGGGACCAAT CCTGTATTCG CTGGGGCTAA CTATGCGGCG TGGGCAGTAA | 850 |
| ACGTTGCGCA AGTTATCGAT AGCGAAACAG CTGATAATTT GGAAAAGACA | 900 |
| ACTGCTGCTC TTTCGATACT TCCTGGTATC GGTAGCGTAA TGGGCATTGC | 950 |
| AGACGGTGCC GTTCACCACA ATACAGAAGA GATAGTGGCA CAATCAATAG | 1000 |
| CTTTATCGTC TTTAATGGTT GCTCAAGCTA TTCCATTGGT AGGAGAGCTA | 1050 |
| GTTGATATTG GTTTCGCTGC ATATAATTTT GTAGAGAGTA TTATCAATTT | 1100 |
| ATTTCAAGTA GTTCATAATT CGTATAATCG TCCCGCGTAT TCTCCGGGGC | 1150 |
| ATAAAACGCA ACCATTTCTT CATGACGGGT ATGCTGTCAG TTGGAACACT | 1200 |
| GTTGAAGATT CGATAATCCG AACTGGTTTT CAAGGGGAGA GTGGGCACGA | 1250 |

```
CATAAAAATT ACTGCTGAAA ATACCCCGCT TCCAATCGCG GGTGTCCTAC      1300

TACCGACTAT TCCTGGAAAG CTGGACGTTA ATAAGTCCAA GACTCATATT      1350

TCCGTAAATG GTCGGAAAAT AAGGATGCGT TGCAGAGCTA TAGACGGTGA      1400

TGTAACTTTT TGTCGCCCTA AATCTCCTGT TTATGTTGGT AATGGTGTGC      1450

ATGCGAATCT TCACGTGGCA TTTCACAGAA GCAGCTCGGA GAAAATTCAT      1500

TCTAATGAAA TTTCGTCGGA TTCCATAGGC GTTCTTGGGT ACCAGAAAAC      1550

AGTAGATCAC ACCAAGGTTA ATTCTAAGCT ATCGCTATTT TTTGAAATCA      1600

AAAGCTGA                                                    1608
```

(2) INFORMATION FOR SEQ ID NO:9:

(i) SEQUENCE CHARACTERISTICS:
        (A) LENGTH: 535 amino acids
        (B) TYPE: amino acid
        (D) TOPOLOGY: linear (ii) MOLECULE TYPE: protein (iii) HYPOTHETICAL:

(iv) ANTI-SENSE:

(ix) FEATURE: (A)NAME:
        (B) LOCATION:

(xi) SEQUENCE DESCRIPTION: SEQ ID NO:9:

```
Gly Ala Asp Asp Val Asp Ser Ser Lys Ser Phe Val Met
1               5                   10

Glu Asn Phe Ser Ser Tyr His Gly Thr Lys Pro Gly Tyr Val
15                  20                  25

Asp Ser Ile Gln Lys Gly Ile Gln Lys Pro Lys Ser Gly Thr
        30                  35                  40

Gln Gly Asn Tyr Asp Asp Asp Trp Lys Gly Phe Tyr Ser Thr
            45                  50                  55

Asp Asn Lys Tyr Asp Ala Ala Gly Tyr Ser Val Asp Asn Glu
                60                  65                  70

Asn Pro Leu Ser Gly Lys Ala Gly Gly Val Val Lys Val Thr
                    75                  80

Tyr Pro Gly Leu Thr Lys Val Leu Ala Leu Lys Val Asp Asn
85              90                      95

Ala Glu Thr Ile Lys Lys Glu Leu Gly Leu Ser Leu Thr Glu
        100                 105                 110

Pro Leu Met Glu Gln Val Gly Thr Glu Glu Phe Ile Lys Arg
            115                 120                 125

Phe Gly Asp Gly Ala Ser Arg Val Val Leu Ser Leu Pro Phe
                130                 135                 140

Ala Glu Gly Ser Ser Ser Val Glu Tyr Ile Asn Asn Trp Glu
                    145                 150

Gln Ala Lys Ala Leu Ser Val Glu Leu Glu Ile Asn Phe Glu
155                 160                 165

Thr Arg Gly Lys Arg Gly Gln Asp Ala Met Tyr Glu Tyr Met
        170                 175                 180

Ala Gln Ala Cys Ala Gly Asn Arg Val Arg Arg Ser Val Gly
            185                 190                 195

Ser Ser Leu Ser Cys Ile Asn Leu Asp Trp Asp Val Ile Arg
                200                 205                 210
```

```
Asp Lys Thr Lys Thr Lys Ile Glu Ser Leu Lys Glu His Gly
            215                 220

Pro Ile Lys Asn Lys Met Ser Glu Ser Pro Asn Lys Thr Val
225                 230                 235

Ser Glu Glu Lys Ala Lys Gln Tyr Leu Glu Glu Phe His Gln
    240                 245                 250

Thr Ala Leu Glu His Pro Glu Leu Ser Glu Leu Lys Thr Val
            255                 260                 265

Thr Gly Thr Asn Pro Val Phe Ala Gly Ala Asn Tyr Ala Ala
                270                 275                 280

Trp Ala Val Asn Val Ala Gln Val Ile Asp Ser Glu Thr Ala
                285                 290

Asp Asn Leu Glu Lys Thr Thr Ala Ala Leu Ser Ile Leu Pro
295                 300                 305

Gly Ile Gly Ser Val Met Gly Ile Ala Asp Gly Ala Val His
    310                 315                 320

His Asn Thr Glu Glu Ile Val Ala Gln Ser Ile Ala Leu Ser
            325                 330                 335

Ser Leu Met Val Ala Gln Ala Ile Pro Leu Val Gly Glu Leu
                340                 345                 350

Val Asp Ile Gly Phe Ala Ala Tyr Asn Phe Val Glu Ser Ile
                355                 360

Ile Asn Leu Phe Gln Val Val His Asn Ser Tyr Asn Arg Pro
365                 370                 375

Ala Tyr Ser Pro Gly His Lys Thr Gln Pro Phe Leu His Asp
    380                 385                 390

Gly Tyr Ala Val Ser Trp Asn Thr Val Glu Asp Ser Ile Ile
            395                 400                 405

Arg Thr Gly Phe Gln Gly Glu Ser Gly His Asp Ile Lys Ile
                410                 415                 420

Thr Ala Glu Asn Thr Pro Leu Pro Ile Ala Gly Val Leu Leu
                425                 430

Pro Thr Ile Pro Gly Lys Leu Asp Val Asn Lys Ser Lys Thr
435                 440                 445

His Ile Ser Val Asn Gly Arg Lys Ile Arg Met Arg Cys Arg
    450                 455                 460

Ala Ile Asp Gly Asp Val Thr Phe Cys Arg Pro Lys Ser Pro
            465                 470                 475

Val Tyr Val Gly Asn Gly Val His Ala Asn Leu His Val Ala
                480                 485                 490

Phe His Arg Ser Ser Ser Glu Lys Ile His Ser Asn Glu Ile
                495                 500

Ser Ser Asp Ser Ile Gly Val Leu Gly Tyr Gln Lys Thr Val
505                 510                 515

Asp His Thr Lys Val Asn Ser Lys Ser Leu Ser Leu Phe Phe Glu
    520                 525                 530

Ile Lys Ser
    535

(2) INFORMATION FOR SEQ ID NO:10:

(i) SEQUENCE CHARACTERISTICS:
        (A) LENGTH: 21 amino acids
        (B) TYPE:   amino acid
```

-continued

```
        (D) TOPOLOGY:  linear (ii) MOLECULE TYPE:  protein (iii) HYPOTHETICAL:

(iv) ANTI-SENSE:

(ix) FEATURE:
         (A) NAME/KEY:
         (B) LOCATION:

(xi) SEQUENCE DESCRIPTION:  SEQ ID NO: 10:
Phe Asn Asn Phe Thr Val Ser Phe Trp Leu Arg Val Pro
1               5                   10

Lys Val Ser Ala Ser His Leu Glu
15                  20
```